(12) United States Patent
Stone et al.

(10) Patent No.: US 8,986,584 B2
(45) Date of Patent: *Mar. 24, 2015

(54) PROCESS FOR MAKING AN EMBOSSED WEB

(75) Inventors: Keith Joseph Stone, Fairfield, OH (US); Roger Dale Young, Ft. Mitchell, KY (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/487,287

(22) Filed: Jun. 4, 2012

(65) Prior Publication Data
US 2012/0248649 A1 Oct. 4, 2012

Related U.S. Application Data

(63) Continuation of application No. 12/721,868, filed on Mar. 11, 2010, now Pat. No. 8,206,628.

(60) Provisional application No. 61/159,906, filed on Mar. 13, 2009.

(51) Int. Cl.
*B29C 59/02* (2006.01)
*A61F 13/15* (2006.01)
(Continued)

(52) U.S. Cl.
CPC ......... *B29C 59/022* (2013.01); *A61F 13/15731* (2013.01); *B26F 1/26* (2013.01); *B29C 55/18* (2013.01); *B29C 59/04* (2013.01);
(Continued)

(58) Field of Classification Search
CPC ...... B29C 59/022; B29C 59/023; B29C 59/04
USPC ......... 264/154, 156, 273, 284, 285, 286, 293, 264/509
See application file for complete search history.

(56) References Cited

U.S. PATENT DOCUMENTS 3,719,736 A 3/1973 Woodruff
3,779,285 A 12/1973 Sinibaldo
(Continued)

FOREIGN PATENT DOCUMENTS

DE 34 39 555 A1 4/1986
EP 0 598 970 A1 6/1994
(Continued)

OTHER PUBLICATIONS

International Search Report & Written Opinion, PCT/US2010/026904, mailed Feb. 7, 2010, 18 pages.
(Continued)

*Primary Examiner* — Timothy Kennedy
(74) *Attorney, Agent, or Firm* — Andrew J. Hagerty

(57) ABSTRACT

A process for making an embossed web. A precursor web is provided between a forming structure and a compliant substrate. The forming structure has a plurality of discrete protruded elements and lands completely surrounding them. Pressure is provided between the compliant substrate and the forming structure to conform the precursor web to the forming structure to form the embossed web. The resulting embossed web has a plurality of discrete extended elements completely surrounded by land areas.

22 Claims, 14 Drawing Sheets

(51) Int. Cl.
| | |
|---|---|
| *B26F 1/26* | (2006.01) |
| *B29C 55/18* | (2006.01) |
| *B29C 65/56* | (2006.01) |
| *B29C 65/00* | (2006.01) |
| *B32B 3/28* | (2006.01) |
| *B32B 7/02* | (2006.01) |
| *B32B 27/20* | (2006.01) |
| *B44C 1/24* | (2006.01) |
| *B29C 59/04* | (2006.01) |
| *B29C 59/06* | (2006.01) |

(52) U.S. Cl.
CPC .............. *B29C 59/06* (2013.01); *B29C 65/56* (2013.01); *B29C 66/21* (2013.01); *B29C 66/45* (2013.01); *B29C 66/81433* (2013.01); *B29C 66/91935* (2013.01); *B29C 66/939* (2013.01); *B29C 66/949* (2013.01); *B31F 2201/0733* (2013.01); *B31F 2201/0738* (2013.01); *B32B 3/28* (2013.01); *B32B 7/02* (2013.01); *B32B 27/20* (2013.01); *B44C 1/24* (2013.01); *B29C 66/9121* (2013.01); *B29C 66/91216* (2013.01); *B29C 66/91411* (2013.01); *B29C 66/9161* (2013.01); *B29C 66/919* (2013.01); *B29C 66/934* (2013.01); *B29C 66/9392* (2013.01)
USPC ........... 264/156; 264/154; 264/273; 264/284; 264/285; 264/286; 264/293; 264/509

(56) References Cited

U.S. PATENT DOCUMENTS

| | | | |
|---|---|---|---|
| 3,911,187 A | | 10/1975 | Raley |
| 3,929,135 A | * | 12/1975 | Thompson .................... 264/154 |
| 4,211,743 A | | 7/1980 | Nauta et al. |
| 4,319,868 A | | 3/1982 | Riemersma et al. |
| 4,343,848 A | | 8/1982 | Leonard |
| 4,546,029 A | | 10/1985 | Cancio et al. |
| 4,695,422 A | | 9/1987 | Curro et al. |
| 4,778,644 A | | 10/1988 | Curro et al. |
| 5,158,819 A | | 10/1992 | Goodman et al. |
| 5,281,371 A | | 1/1994 | Tamura et al. |
| 5,650,215 A | | 7/1997 | Mazurek et al. |
| 5,670,110 A | | 9/1997 | Dirk et al. |
| 5,814,390 A | * | 9/1998 | Stokes et al. .................. 428/181 |
| 5,858,515 A | | 1/1999 | Stokes et al. |
| 5,891,544 A | * | 4/1999 | Chappell et al. ................ 428/76 |
| 5,945,196 A | | 8/1999 | Rieker et al. |
| 6,045,894 A | | 4/2000 | Jonza et al. |
| H1927 H | | 12/2000 | Chen et al. |
| 6,531,230 B1 | | 3/2003 | Weber et al. |
| 6,719,742 B1 | | 4/2004 | McCormack et al. |
| 6,788,463 B2 | | 9/2004 | Merrill et al. |
| 6,797,366 B2 | | 9/2004 | Hanson et al. |
| 6,846,445 B2 | | 1/2005 | Kim et al. |
| 7,037,569 B2 | | 5/2006 | Curro et al. |
| 7,172,801 B2 | | 2/2007 | Hoying et al. |
| 7,303,861 B2 | | 12/2007 | Gray et al. |
| 7,402,723 B2 | | 7/2008 | Stone et al. |
| 7,642,207 B2 | | 1/2010 | Boehmer et al. |
| 7,799,254 B2 | | 9/2010 | Harvey et al. |
| 8,241,543 B2 | | 8/2012 | O'Donnell et al. |
| 2001/0014796 A1 | | 8/2001 | Mizutani et al. |
| 2002/0154406 A1 | | 10/2002 | Merrill et al. |
| 2003/0187170 A1 | | 10/2003 | Burmeister |
| 2003/0201582 A1 | | 10/2003 | Gray et al. |
| 2003/0228445 A1 | | 12/2003 | Vaughn et al. |
| 2004/0046290 A1 | | 3/2004 | Kim et al. |
| 2004/0122395 A1 | | 6/2004 | Stone et al. |
| 2004/0126531 A1 | * | 7/2004 | Harvey et al. ................. 264/284 |
| 2004/0131820 A1 | | 7/2004 | Turner et al. |
| 2004/0161586 A1 | | 8/2004 | Cree et al. |
| 2004/0209041 A1 | | 10/2004 | Muth et al. |
| 2005/0019530 A1 | | 1/2005 | Merrill et al. |
| 2005/0191496 A1 | | 9/2005 | Gray et al. |
| 2005/0279470 A1 | | 12/2005 | Redd et al. |
| 2006/0087053 A1 | | 4/2006 | O'Donnell et al. |
| 2006/0286343 A1 | | 12/2006 | Curro et al. |
| 2007/0062658 A1 | | 3/2007 | Wiwi et al. |
| 2007/0261224 A1 | | 11/2007 | McLeod |
| 2008/0200320 A1 | | 8/2008 | Buckner et al. |
| 2008/0264275 A1 | | 10/2008 | Wilhelm et al. |
| 2009/0155540 A1 | | 6/2009 | Merrill et al. |
| 2012/0105957 A1 | | 5/2012 | Merrill et al. |

FOREIGN PATENT DOCUMENTS

| | | |
|---|---|---|
| GB | 1 344 054 A | 1/1974 |
| JP | 2004-062055 B2 | 6/2004 |
| WO | WO-97/13633 | 4/1997 |
| WO | WO-2007/069964 A1 | 6/2007 |
| WO | WO 2008/120959 A1 | 10/2008 |

OTHER PUBLICATIONS

Nagarajan, Abbott, Yao; Rubber-Assisted Embossing Process; School of Polymer, Textile & Fiber Eng., Georgia Institute of Technology, Atlanta, GA 30332; ANTEC (2007) vol. 5, pp. 2921-2925, 5 pages.

Chang, Yang; Gas pressurized hot embossing for transcription of micro-features; Microsystem Technologies (2003) vol. 10, pp. 76-80, 5 pages; Springer-Verlag.

Dreuth, Heiden; Thermoplastic structuring of thin polymer films; Sensors and Actuators (1999) vol. 78, pp. 198-204, 7 pages; Institute of Applied Physics, University of Giessen, Heinrich-Buff-Ring 16 D-35392 Giessen, Germany; Elsevier Science S.A.

Heckele, Schomburg; Review on micro molding of thermoplastic polymers; Institute of Physics Publishing; Journal of Micromechanics and Microengineering (2004) vol. 14, No. 3, pp. R1-R14, 14 pages; IOP Publishing Ltd.

Kimerling, Liu, Kim, Yao; Rapid hot embossing of polymer microfeatures; Microsystem Technologies (2006) Vol, 12, No, 8, pp. 730-735, 6 pages; School of Polymer, Textile and Fiber Eng., Georgia Institute of Technology, Atlanta GA 30332.

Nagarajan, Yao, Ellis, Azadegan; Through-Thickness Embossing Process for Fabrication of Three-Dimensional Thermoplastic Parts; School of Polymer, Textile & Fiber Eng., Georgia Institute of Technology, Atlanta GA 30332 and Delphi Research Labs, Shelby Township, Michigan 48315; Polymer Engineering and Science (2007) vol. 47, No. 12, pp. 2075-2084, 10 pages.

Rowland, King; Polymer deformation and filling modes during microembossing; Woodruff School of Mechanical Engineering, Georgia Institute of Technology, Atlanta, GA 30329-0405; Institute of Physics Publishing; Journal of Micromechanics and Microengineering (2004) vol. 14, No. 12, pp. 1625-1632, 8 pages; IOP Publishing Ltd.

Truckenmuller, Giselbrecht; Microthermoforming of flexible, not-buried hollow microstructures for chip-based life sciences applications; IEE Proceedings-Nanobiotechnology (Aug, 2004) vol. 151, No. 4, pp. 163-166; 4 pages.

Yao, Nagarajan; Cold Forging Method for Polymer Microfabrication; Department of Mechanical Engineering, Oakland University, Rochester, MI 48309; Polymer Engineering and Science (Oct. 2004) vol. 44, No. 10, pp. 1998-2004, 7 pages.

Yao, Nagarajan, Li, Yi; A Two-Station Embossing Process for Rapid Fabrication of Surface Microstructures on Thermoplastic Polymers; School of Polymer, Textile & Fiber Eng., Georgia Institute of Technology, Atlanta, GA 30332 and Department of Industrial, Welding and Systems Engineering, The Ohio State University, Columbus, OH 43210; Polymer Engineering and Science (2007) vol. 47, No. 4, pp. 530-539, 10 pages; Wiley InterScience; Society of Plastics Engineers.

Yao, Kuduva-Raman-Thanumoorthy; An enlarged process window for hot embossing; School of Polymer, Textile & Fiber Eng., Georgia Institute of Technology, Atlanta, GA 30332; Journal of Micromechanics and Microengineering (2008) vol. 18, pp. 1-7; 7 pages; IOP Publishing Ltd.

* cited by examiner

PROCESS FOR MAKING AN EMBOSSED WEB

CROSS REFERENCE TO RELATED APPLICATION

This application is a continuation of U.S. application Ser. No. 12/721,868, filed Mar. 11, 2010, now U.S. Pat. No. 8,206,628 published as U.S. Application Publication No. 2010/0230858, and claims the benefit of U.S. Provisional Application No. 61/159,906, filed Mar. 13, 2009.

FIELD OF THE INVENTION

The present invention relates to a process for making an embossed web comprising a plurality of discrete extended elements.

BACKGROUND OF THE INVENTION

Web materials, such as thermoplastic films, have a variety of uses including component materials of absorbent articles (such as topsheets and backsheets), packaging (such as flow wrap, shrink wrap, and polybags), trash bags, food wrap, dental floss, wipes, electronic components, and the like. For many of these uses of web materials, it can be beneficial for the web material to have a textured surface which can provide the surface of the web material with a desirable feel, visual impression, and/or audible impression.

Polymeric webs exhibiting a soft and silky tactile impression can be made via a vacuum forming process or a hydroforming process. With a typical vacuum forming process, a precursor web is heated and placed over a forming structure. Then a vacuum of air forces the precursor web to conform to the texture of the forming structure. The resulting polymeric web has texture that can provide a soft and silky tactile impression, depending upon the texture of the forming structure. While a vacuum forming process can be suitable for making a soft and silky polymeric web, a vacuum forming process is typically limited with respect to the amount of pressure capable of being exerted onto a precursor web. As a result, it is usually required to heat a precursor film to significantly soften or melt the precursor film prior to placement on the forming structure in order to vacuum form the precursor film to the forming structure. A vacuum forming process is therefore an inefficient process due to the heating step and the limited pressures generated by the process.

With a typical hydroforming process, a precursor web is placed over a forming structure and high pressure and high temperature water jets force the precursor web to conform to the texture of the forming structure. The resulting polymeric web can have texture that can provide a soft and silky tactile impression, depending upon the texture of the forming structure. A hydroforming process, although capable of producing soft and silky polymeric webs, is typically a costly and inefficient process involving the use of high pressure and high temperature water jets and subsequent drying steps, including dewatering steps.

Embossing is a process that typically involves the act of mechanically working a substrate to cause the substrate to conform under pressure to the depths and contours of a pattern engraved or otherwise formed on an embossing roll. It is widely used in the production of consumer goods. Manufacturers use the embossing process to impart a texture or relief pattern into products made of textiles, paper, synthetic materials, plastic materials, metals, and wood.

Embossing processes have been used to provide texture to polymeric films. However, such embossing processes typically require extruding a molten resin onto a forming structure or heating a precursor web before placement onto a forming structure and then embossing to produce an embossed web. The embossed web is then cooled, typically by cooling the embossing rolls or plates used to emboss the heated precursor web or molten resin. The cooling step is often utilized to set the texture in the embossed web. However, these heating and cooling steps add undesirable cost and inefficiency, as well as complexity, to the process. In addition, such embossing processes typically involve relatively large dwell times, which can result in slow, inefficient processes.

It is also typically difficult to impart relatively small scale texture to precursor webs using conventional embossing processes. Furthermore, typical embossing processes tend to produce embossed webs having relatively uniform thickness throughout the web.

Despite the knowledge in the art, there remains a desire to develop a more efficient process for making embossed webs that have desirable feel, visual impression, and/or audible impression, especially embossed webs exhibiting thinning in desirable areas of the embossed web. In certain aspects, a desired process is efficient with respect to the energy and resources required by the process. In certain aspects, a desired process is capable of running at high speeds. In certain aspects, a desired process is capable of running at relatively low temperatures, such as ambient temperature.

SUMMARY OF THE INVENTION

The present invention relates to a process for making an embossed web comprising a plurality of discrete extended elements. The process comprises: (a) providing a forming structure comprising a plurality of discrete protruded elements and lands completely surrounding the discrete protruded elements; (b) providing a compliant substrate; and (c) providing a base web between the forming structure and the compliant substrate; and (d) providing pressure between the compliant substrate and the forming structure sufficient to conform the base web about the discrete protruded elements of the forming structure to form the embossed web.

In one embodiment, the present invention encompasses a process for making an embossed web comprising a plurality of discrete extended elements formed integrally with said embossed web, said extended elements having open proximal portions, closed or open distal ends, and sidewalls, said extended elements being thinned at said distal ends and/or along said sidewalls, said process comprising the steps of: (a) providing a forming structure comprising a plurality of discrete protruded elements and lands completely surrounding said discrete protruded elements, wherein said discrete protruded elements each have a diameter of less than about 500 microns; (b) providing a compliant substrate; (c) providing a precursor web between said compliant substrate and said forming structure; wherein said precursor web comprises synthetic material, metallic material, biological material, or combinations thereof; and (d) providing pressure between said compliant substrate and said forming structure sufficient to conform said precursor web to said discrete protruded elements of said forming structure to form said embossed web.

In another embodiment, the present invention encompasses a process for making an embossed web comprising a plurality of discrete extended elements formed integrally with said embossed web, said extended elements having open proximal portions, closed or open distal ends, and sidewalls, said extended elements being thinned at said distal ends and/or along said sidewalls, said process comprising the steps of: (a) providing a forming structure comprising a plurality of discrete protruded elements and lands completely surrounding said discrete protruded elements, wherein said forming structure comprises at least about 95 discrete protruded elements per square centimeter; (b) providing a compliant substrate; (c) providing a precursor web between said compliant substrate and said forming structure; wherein said precursor web comprises synthetic material, metallic material, biological material, or combinations thereof; and (d) providing pressure between said compliant substrate and said forming structure sufficient to conform said precursor web to said discrete protruded elements of said forming structure to form said embossed web.

In another embodiment, the present invention encompasses a process for making an embossed web comprising a plurality of discrete extended elements formed integrally with said embossed web, said extended elements having open proximal portions and closed or open distal ends, said extended elements being thinned at or near said distal ends, said process comprising the steps of: (a) providing a forming structure comprising a plurality of discrete protruded elements and lands completely surrounding said discrete protruded elements, wherein said discrete protruded elements each have a non-columnar shape; (b) providing a compliant substrate; (c) providing a precursor web between said compliant substrate and said forming structure; wherein said precursor web comprises synthetic material, metallic material, biological material, or combinations thereof; and (d) providing pressure between said compliant substrate and said forming structure sufficient to conform said precursor web to said discrete protruded elements of said forming structure to form said embossed web.

In another embodiment, the present invention encompasses a process for making an embossed web comprising a plurality of discrete extended elements formed integrally with said embossed web, said extended elements having open proximal portions and closed or open distal ends, said extended elements being thinned at or near said distal ends, said process comprising the steps of: (a) providing a forming structure comprising a plurality of discrete protruded elements and lands completely surrounding said discrete protruded elements, wherein said discrete protruded elements have an average height; (b) providing a compliant substrate having a Shore A hardness of from about 30 to about 80 durometer; (c) providing a precursor web between said compliant substrate and said forming structure, wherein said precursor web comprises synthetic material, metallic material, biological material, or combinations thereof, and wherein said precursor web has a thickness; (d) providing pressure between said compliant substrate and said forming structure sufficient to conform said precursor web to said discrete protruded elements of said forming structure to form said embossed web; and (e) wherein a ratio of said average height of said protruded elements to said thickness of said precursor web is at least about 2:1.

DETAILED DESCRIPTION OF THE INVENTION

The present invention encompasses a process for making an embossed web comprising: (a) providing a forming structure comprising a plurality of discrete protruded elements and lands completely surrounding the discrete protruded elements; (b) providing a compliant substrate; (c) providing a precursor web between the forming structure and the compliant substrate; and (d) providing pressure between the compliant substrate and the forming structure sufficient to conform the precursor web about the discrete protruded elements of the forming structure to form the embossed web.

Forming Structure

A forming structure useful in the process of the present invention comprises a plurality of discrete protruded elements and lands completely surrounding the discrete protruded elements. The discrete protruded elements of the forming structure of the present invention are small in scale relative to typical patterns used on dies in embossing processes. The discrete protruded elements of the forming structure also have relatively high aspect ratios. This combination of properties can allow the process of the invention to produce embossed webs comprising relatively high aspect ratio extended elements with thinned distal ends, even without heating the precursor web and even at high speeds.

Figure 1:
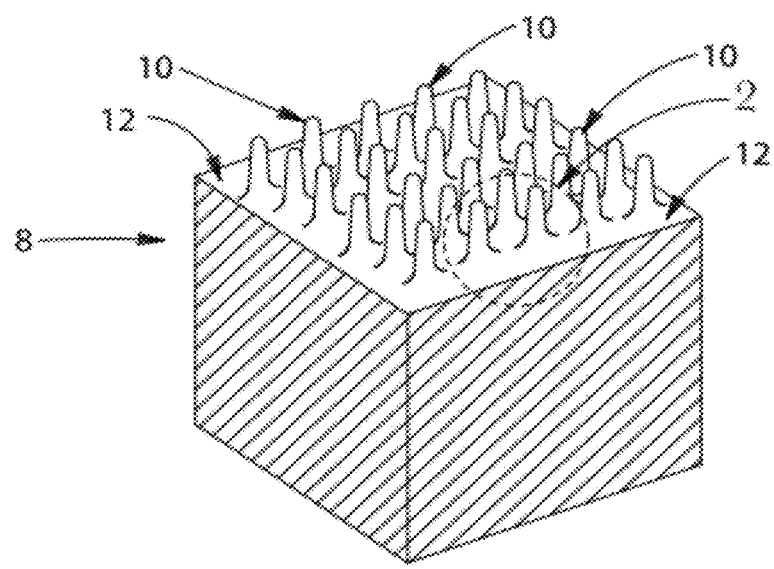
FIG. 1 is a perspective view of a portion of a forming structure of the present invention.

A forming structure of the present invention, such as the forming structure 8 referred to with respect to FIG. 1, is used for making an embossed web in the process of the present invention. The forming structure is sometimes referred to as a forming screen. FIG. 1 shows a portion of a forming structure 8 of the present invention in partial perspective view. Discrete protruded elements 10 of FIG. 1 extend from forming structure first surface 12 and have generally columnar, pillar-like forms.

Figure 2:
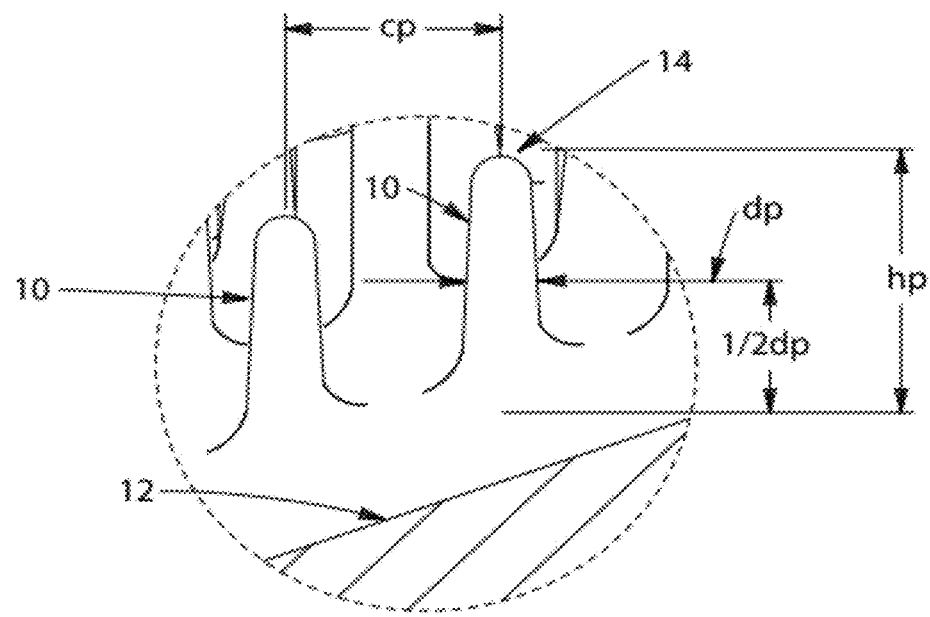
FIG. 2 is an enlarged perspective view of a portion of the forming structure shown in FIG. 1.
Figure 7:
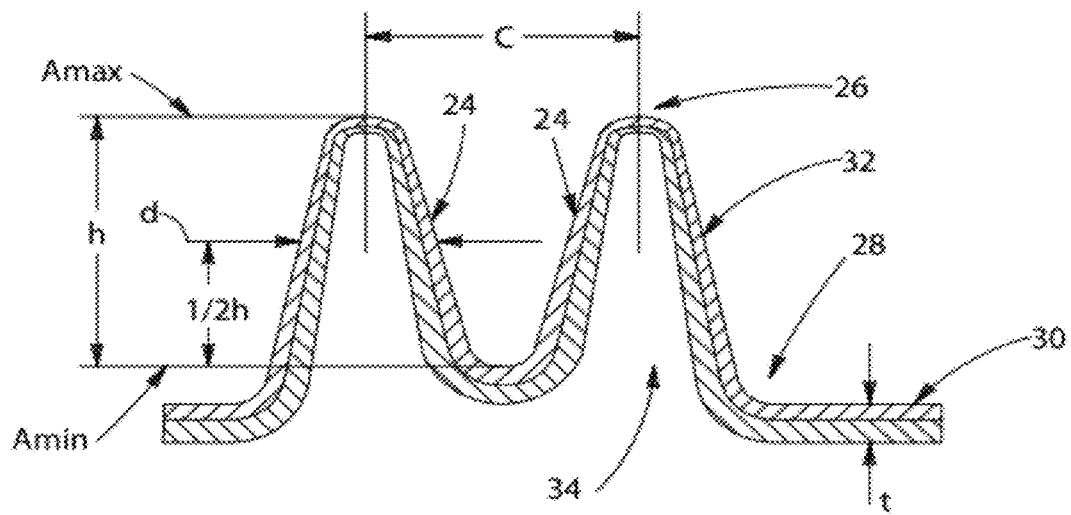
FIG. 7 is a cross-sectional view of a portion of an embossed web of the present invention.

FIG. 2 is a further enlarged, partial perspective view of the forming structure 8 shown in FIG. 1, and compares with the similar view of embossed web 18 in FIG. 7. The discrete protruded elements 10 can be made by methods described below to extend from first surface 12 to a distal end 14. As shown in FIG. 2, the discrete protruded elements 10 can have a height ("hp") measured from a minimum amplitude measured from first surface 12 between adjacent protrusions to distal end 14. As such, the first surface 12 constitutes a land area that completely surrounds the discrete protruded elements 10. Protruded element height hp can be at least about 30 microns, at least about 50 microns, at least about 75 microns, at least about 100 microns, at least about 150 microns, at least about 250 microns, or at least about 380 microns. Protruded elements 10 have a diameter ("dp"), which for a generally cylindrical structure is the outside diameter. For non-uniform cross-sections, and/or non-cylindrical structures of protruded elements 10, diameter dp is measured as the average cross-sectional dimension of protruded elements at ½ the height hp of the protruded elements 10, as shown in FIG. 2. Protruded elements can have a diameter dp that can be from about 10 microns to about 5,000 microns. Other suitable diameters include, for example, of about 50 microns to about 500 microns, about 65 microns to about 300 microns, about 75 microns to about 200 microns, about 100 microns to about 25,000 microns, about 500 microns to about 5000 microns, or about 800 microns to about 2,500 microns. In certain embodiments, the protruded elements can have larger diameters for forming macro-scale discrete extended elements. For example, the protruded elements can have diameters up to about 2.5 centimeters, up to about 2 centimeters, up to about 1.5 centimeters, up to about 1 cm, up to about 0.5 centimeters, or up to about 0.1 centimeters. In one embodiment, the protruded elements of the forming structure will have a diameter of less than about 500 microns, or less than about 300 microns.

For each protruded element 10, a protruded element aspect ratio, defined as hp/dp, can be determined. Protruded elements 10 can have an aspect ratio hp/dp of at least about 0.5, at least about 0.75, at least about 1, at least about 1.5, at least about 2, at least about 2.5, or at least about 3 or higher. The protruded elements 10 can have a center-to-center spacing Cp between two adjacent protruded elements 10 of from about 100 microns to about 1,020 microns, from about 100 microns to about 640 microns, from about 150 microns to about 500 microns, or from about 180 microns to about 430 microns.

In general, it is believed that the actual distance between two adjacent protruded elements 10 (i.e., an "edge-to-edge" dimension) should be greater than twice the thickness t of precursor web to ensure adequate deformation of precursor web between adjacent protruded elements 10. The discrete protruded elements 10 will typically have an edge-to-edge spacing of from about 30 microns to about 800 microns, from about 30 microns to about 650 microns, from about 50 microns to about 500 microns, or from about 60 to about 300 microns.

In general, the forming structure of the present invention, for a given portion of the forming structure, will comprise at least about 95 discrete protruded elements per square centimeter, at least about 240 discrete protruded elements per square centimeter, from about 350 to about 10,000 discrete protruded elements per square centimeter, from about 500 to about 5,000 discrete protruded elements per square centimeter, or from about 700 to about 3,000 discrete protruded elements per square centimeter.

In certain embodiments, given portions of the forming structure can comprise area densities of discrete protruded elements as described in the preceding paragraph, and other portions of the forming structure that comprise no discrete protruded elements at all. In other embodiments, the discrete protruded elements of the forming structure can be located in different horizontal planes of the forming structure.

In general, because the actual height hp of each individual protruded element 10 may vary, an average height ("$hp_{avg}$") of a plurality of protruded elements 10 can be determined by determining a protruded element average minimum amplitude ("$Ap_{min}$") and a protruded element average maximum amplitude ("$Ap_{max}$") over a predetermined area of forming structure 8. Likewise, for varying cross-sectional dimensions, an average protrusion diameter ("$dp_{avg}$") can be determined for a plurality of protrusions 8. Such amplitude and other dimensional measurements can be made by any method known in the art, such as by computer aided scanning microscopy and related data processing. Therefore, an average aspect ratio of the protruded elements 10, ("$ARp_{avg}$") for a predetermined portion of the forming structure 8 can be expressed as $hp_{avg}/dp_{avg}$. The dimensions hp and dp for protruded elements 10 can be indirectly determined based on the known specifications for making forming structure 8, as disclosed more fully below.

In one embodiment, a ratio of the average height $hp_{avg}$ of the discrete protruded elements to the thickness of the precursor web is at least about 2:1, at least about 3:1, at least about 4:1, or at least about 5:1. This ratio can be important to ensure the precursor web is stretched enough so that it becomes permanently deformed to create an embossed web of the present invention, especially at desirable process conditions and speed.

Figure 3:
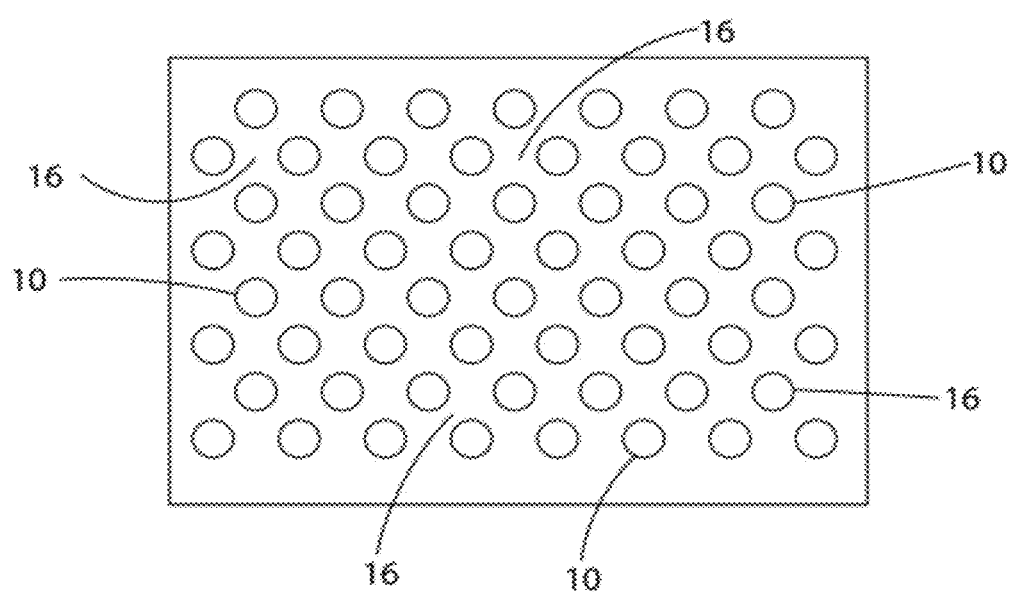
FIG. 3 is a top view of a forming structure of the present invention.

FIG. 3 is a top view of one embodiment of a forming structure of the present invention. The forming structure comprises a plurality of discrete protruded elements 10 that are completely surround by land area 16.

The discrete protruded elements of the forming structure can have distal ends that are flat, rounded or sharp, depending upon whether it is desired to produce an embossed web having discrete extended elements with distal ends that are open (requiring a sharper protruded element on the forming structure) or closed (requiring a more rounded protruded element on the forming structure). The rounded distal ends of the discrete protruded elements of the forming structure can have a certain tip radius, such as from about 5 microns to about 150 microns, from about 10 microns to about 100 microns, from about 20 to about 75 microns, or from about 30 microns to about 60 microns.

The sidewalls of the discrete protruded elements can be completely vertical or can be tapered. In one embodiment, the discrete protruded elements have tapered sidewalls, as tapered sidewalls can have an impact on durability and longevity of the compliant substrate of the present invention by easing the compression or tension on compliant substrate as it conforms around discrete protruded elements of the forming structure. This can also allow the web to more easily separate from the forming structure after embossing. In one embodiment, the sidewalls will typically have a degree of taper of from about 0° to about 50°, from about 2° to about 30°, or from about 5° to about 25°.

Figure 4:
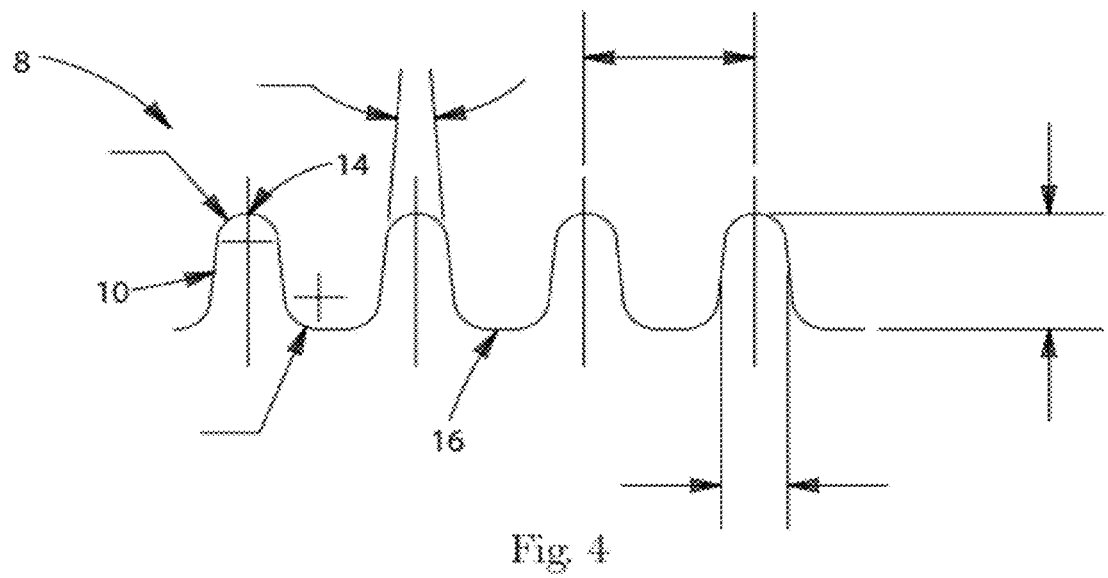
FIG. 4 is a side view of protruded elements of a forming structure of the present invention.

FIG. 4 shows a cross-sectional view of one embodiment of discrete protruded elements 10 of a forming structure 8, wherein the round distal ends 14 of the discrete protruded elements 10 have a tip radius of about 46 microns (0.0018 inch). The sidewalls of the discrete protruded elements 10 have a degree of taper of about 11°.

Figure 5:
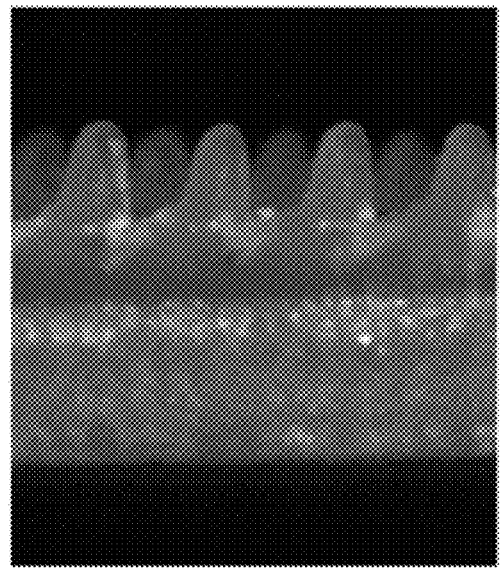
FIG. 5 is a photomicrograph showing a side view of a forming structure of the present invention.

FIG. 5 is a photomicrograph of a forming structure comprising a plurality of discrete protruded elements having dimensions as depicted in FIG. 4.

In one embodiment the diameter of protruded elements 10 is constant or decreases with increasing amplitude. As shown in FIG. 2, for example, the diameter, or largest lateral cross-sectional dimension, of protruded elements 10 is a maximum near first surface 12 and steadily decreases to distal end 14. This structure is believed to be desirable to help ensure that the embossed web can be readily removed from the forming structure 8.

The discrete protruded elements of the forming structure can be comprised of a variety of different shapes, such as generally columnar or non-columnar shapes, including circular, oval, square, triangular, hexagonal, trapezoidal, ridges, pyramids, hour-glass shaped, and the like, and combinations thereof.

Forming structure 8 can be made of any material that can be formed to have protruded elements 10 having the necessary dimensions to make an embossed web of the present invention, is dimensionally stable over process temperature ranges experienced by forming structure 8, has a tensile modulus of at least about 30 MPa, at least about 100 MPa, at least about 200 MPa, at least about 400 MPa, at least about 1,000 MPa, or at least about 2,000 MPa; a yield strength of at least about 2 MPa, at least about 5 MPa, at least about 10 MPa, or at least about 15 MPa; and a strain at break of at least about 1%, at least about 5%, or at least about 10%. It has been found that relatively tall, high aspect ratio protruded elements form better embossed webs as the modulus of the material of the forming structure increases, as long as it has sufficient strain at break (i.e., not too brittle) so as not to break. For modulus and yield strength data, values can be determined by testing according to known methods, and can be tested at standard TAPPI conditions at a strain rate of 100%/minute.

In one embodiment, protruded elements 10 are made integrally with forming structure 8. That is, the forming structure is made as an integrated structure, either by removing material or by building up material. For example, forming structure 8 having the required relatively small scale protruded elements 10 can be made by local selective removal of material, such as by chemical etching, mechanical etching, or by ablating by use of high-energy sources such as electrical-discharge machines (EDM) or lasers, or by electron beam (e-beam), or by electrochemical machining (ECM). In one embodiment, the forming structure may be constructed by a photo etched laminate process generally in accordance with the teachings of U.S. Pat. No. 4,342,314.

In one method of making forming structure 8, a base material susceptible to laser modification is laser "etched" to selectively remove material to form protruded elements 10. By "susceptible to laser modification", it is meant that the material can be selectively removed by laser light in a controlled manner, recognizing that the wavelength of light used in the laser process, as well as the power level, may need to be matched to the material (or vice-versa) for optimum results. Laser etching can be achieved by known laser techniques, selecting wavelength, power, and time parameters as necessary to produce the desired protruded element dimensions. Currently known materials susceptible to laser modification include thermoplastics such as polypropylene, acetal resins such as DELRIN® from DuPont, Wilmington Del., USA, thermosets such as crosslinked polyesters, or epoxies, or even metals such as aluminum, copper, brass, nickel, stainless steel, or alloys thereof. Optionally, thermoplastic and thermoset materials can be filled with particulate or fiber fillers to increase compatibility with lasers of certain wavelengths of light and/or to improve modulus or toughness to make more durable protruded elements 10. For example, certain polymers, such as PEEK, can be laser machined to higher resolution and at higher speeds by uniformly filling the polymer with sufficient amounts of hollow carbon nanotube fibers.

In one embodiment a forming structure can be laser machined in a continuous process. For example, a polymeric material such as DELRIN® can be provided in a cylindrical form as a base material having a central longitudinal axis, an outer surface, and an inner surface, the outer surface and inner surface defining a thickness of the base material. It can also be provided as a solid roll. A moveable laser source can be directed generally orthogonal to the outer surface. The moveable laser source can be moveable in a direction parallel to the central longitudinal axis of the base material. The cylindrical base material can be rotated about the central longitudinal axis while the laser source machines, or etches, the outer surface of the base material to remove selected portions of the base material in a pattern that defines a plurality of discrete protruded elements. Each protruded element can have a generally columnar and pillar-like shape, as disclosed herein. By moving the laser source parallel to the longitudinal axis of the cylindrical base material as the cylindrical base material rotates, the relative movements, i.e., rotation and laser movement, can be synchronized such that upon each complete rotation of cylindrical base material a predetermined pattern of protruded elements can be formed in a continuous process similar to "threads" of a screw.

The forming structure of the present invention can be in the form of a flat plate, a roll, a belt, a sleeve, or the like. In one embodiment, the forming structure is in the form of a roll.

The bottom surface of the forming structure can be, for example, porous or non-porous. For example, the bottom surface can include an opening, having a width small enough so that the precursor web does not deform into the opening, which vents the forming structure by allowing air to pass through the forming structure. In one embodiment, a means is provided to allow any air trapped under the web to escape. For example, a vacuum assist can be provided to remove the air under the web, for example by pulling the air through the vent openings in the forming structure, so as not to increase the required pressure needed to produce the embossed web.

The forming structure of the present invention can optionally further comprise depressions or apertures. If the forming structure further comprises depressions or apertures, when used in combination with a compliant substrate in a process of the present invention, the precursor web can be forced into the depressions or apertures of the forming structure by the compliant substrate, such that discrete extended elements can be formed in the precursor web extending from the surface of the precursor web opposite the surface from which the discrete protruded elements are formed by the protruded elements of the forming structure. As a result, a two-sided embossed web can be created, having different patterns or dimensions of extended elements on each side of the embossed web. Depending upon the pressure generated between the forming structure and compliant substrate, as well as the geometric shapes of the protruded elements and optional depressions or apertures of the forming structure, the discrete extended elements of the embossed web can have closed or open distal ends.

Compliant Substrate

A compliant substrate is utilized in the process of the present invention to provide a force against the forming structure. At a minimum, the outer surface of the compliant substrate (i.e. the surface of the compliant substrate oriented towards the forming structure) comprises a compliant material. For example, the compliant substrate can comprise a rigid material covered by a compliant material. The rigid material can be a metal (such as steel), a plastic, or any other material that is significantly harder than the compliant material. The thickness of the compliant material covering the rigid material will typically be no greater than about 26 mm, from about 1 mm to about 26 mm, or from about 1 mm to about 7 mm. Alternatively, the entire compliant substrate can be made of a compliant material.

The compliant substrate or compliant material can include elastomers, felts, liquid-filled bladders, and combinations thereof. In one embodiment, the compliant substrate comprises a porous elastomer. The compliant substrate, or the compliant material utilized in the compliant substrate, preferably has resilient properties (such as compression recovery) such that the compliant material rebounds fast enough to facilitate the process of the present invention, especially a continuous process.

The compliant substrate, or the compliant material utilized in the compliant substrate, preferably also has enough durability to emboss large quantities of precursor web material. As a result, the compliant substrate needs to have a suitable degree of abrasion resistance, wherein the compliant substrate will tend to be abraded by the forming structure during the process.

The compliant substrate can be in the form of a flat plate, a roll, a belt, a sleeve, or the like. In one embodiment, the compliant substrate is a metal roll covered with a compliant material, such as rubber. In another embodiment, the compliant substrate and the forming structure are both in the form of rolls. In another embodiment, the compliant substrate is a roll that has a diameter greater than the diameter of the forming structure roll. In another embodiment, the compliant substrate is a roll that has a diameter less than the diameter of the forming structure roll. In another embodiment, the compliant substrate roll has a diameter that is the same as the diameter of the forming structure roll.

The compliant substrate, or the compliant material utilized in the compliant substrate, will typically have a hardness of from about 30 to about 80 durometer, from about 30 to about 60 durometer, from about 30 to about 50 durometer, or from about 60 to about 80 durometer, on the Shore A scale. Hardness on the Shore A scale is typically determined by using an ASTM D2240 durometer, such as the Model 306 Type A Classic Style Durometer available from PTC Instruments of Los Angeles, Calif. It should be recognized that the compliant substrate can exhibit varying hardness, for example lower hardness near the outer surface and higher hardness towards the inner surface of the compliant substrate (i.e. varying hardness in the z-direction of the compliant substrate) or varying hardness across the outer surface of the compliant substrate (i.e. varying hardness in the x-y plane of the compliant substrate).

The compliant material utilized in the compliant substrate will typically have a tensile modulus of from about 1 to about 20 MPa, from about 2 to about 18 MPa, or from about 4 to about 15 MPa. The tensile modulus of the compliant material can be determined at a strain rate of $0.1\ \text{sec}^{-1}$.

Non-limiting examples of suitable compliant materials include natural rubber, urethane rubber, polyurethane rubber, chlorosulfonated polyethylene rubber (available under the tradename HYPALON® from DuPont), chloroprene rubber, norbornene rubber, nitrile rubber, hydrogenated nitrile rubber, styrene rubber, styrene-butadiene rubber, butadiene rubber, silicone rubber, ethylene-propylene-diene ("EPDM") rubber, isobutylene-isoprene rubber, felt (such as pressed wool felt), and the like. Particularly useful compliant materials are isoprene, EPDM, neoprene, and HYPALON® having a Shore A hardness of from about 30 to about 50 durometer, from about 40 to about 70 durometer, or from about 60 to about 80 durometer.

In certain embodiments, such as in a continuous high speed process, compliant materials that have higher Shore A hardness and lower thicknesses can be beneficial. In one embodiment, the compliant material has a Shore A hardness of from about 70 to about 80 durometer and a thickness of from about 1 mm to about 5 mm.

Other suitable compliant materials include regeneratable compliant materials such as leather or self-healing compliant materials. For example, leather can be wetted and dried to "recharge" the leather after it has been used for a period of time in a process such as those disclosed herein. Self-healing compliant materials can include self-healing rubber based on supramolecular chemistry, such as those available from Arkema under the trade name Reverlink.

The compliant material can also be a material, such as an absorbent core, that can be fed between a rigid material and the forming structure along with a precursor web. Such a material can serve to generate pressure against the precursor web and forming structure so as to emboss the precursor web. Such a material can then be later incorporated, along with the embossed web, into a finished consumer product, such as a feminine hygiene product.

The compliant substrate can optionally comprise recessed regions of a depth sufficient to prevent the embossing of the precursor web in the particular region, or only minimally emboss the precursor web in the particular region, during the process of the present invention. The optional recessed regions of the compliant substrate can be in the form of a specific pattern or design, such as a flower, bird, ribbon, wave, cartoon character, logo, and the like, so that the embossed web will have an unembossed region that stands out visually from, and/or has a different hand feel than, the embossed regions of the embossed web.

Precursor Web

A precursor web is converted into an embossed web according to the process of the present invention. Suitable precursor webs include materials that can be deformed by pressure generated between the forming structure and the compliant substrate of the present invention, such that the precursor web is able to be conformed to the topography of the forming structure to produce an embossed web.

The precursor web of the present invention typically comprises synthetic material, metallic material, biological material (in particular, animal-derived materials), or combinations thereof. The precursor web can optionally comprise cellulosic material. In one embodiment, the precursor web is free of cellulosic material. Non-limiting examples of suitable precursor webs include polymeric films, metallic foils (e.g. aluminum, brass, copper, and the like), webs comprising sustainable polymers, foams, fibrous nonwoven webs comprising synthetic fibers (e.g. TYVEK®), collagen films, chitosan films, rayon, cellophane, and the like. Suitable precursor webs further include laminates or blends of these materials.

If the precursor is a fibrous web, the fibrous web typically will have a high density such that it behaves similar to a film material. One example of such a high density fibrous web is TYVEK®.

In one embodiment, the precursor web is a polymeric film. Suitable polymeric films include thermoplastic films such as polyethylene, polypropylene, polystyrene, polyethylene terephthalate (PET), polymethylmethacrylate (PMMA), polyvinyl alcohol (PVA), nylon, polytetrafluoroethylene (PTFE) (e.g., TEFLON), or combinations thereof. Suitable polyermic films can comprise blends or mixtures of polymers.

In certain embodiments, the precursor web can be a web comprising a sustainable polymer, such as polylactides, polyglycolides, polyhydroxyalkanoates, polysaccharides, polycaprolactones, and the like, or mixtures thereof.

The thickness of the precursor web prior to embossing will typically range from about 5 to about 300 microns, about 5 microns to about 150 microns, about 5 microns to about 100 microns, or about 15 microns to about 50 microns. Other suitable thicknesses includes about 1, 2, 3, 4, 5, 6, 7, 8, 9, 10, 20, 30, 40, 50, 60, 70, 80, 90, 100, 150, 200, 250, or 300 microns.

Precursor webs, such as polymeric webs, will typically have a glass transition temperature of about −100° C. to about 120° C., or about −80° C. to about 100° C., or other suitable ranges. Precursor webs, such as polymeric webs, can have a melting point of about 100° C. to about 350° C. For example, a precursor web formed of LDPE or a blend of LDPE and LLDPE has a melting pointing of about 110° C. to about 122° C. A precursor web formed of polypropylene has a melting point of about 165° C. A precursor web formed of polyester has a melting point of about 255° C. A precursor web formed of Nylon 6 has a melting point of about 215° C. A precursor web formed of PTFE has a melting point of about 327° C.

In one embodiment, the process is carried out at a temperature less than the melting point of the precursor web. For example, the process can be carried out at 10° C. less than the melting point of the precursor web. In another embodiment, the process is carried out at a temperature substantially equal to the melting point of the precursor web. In one embodiment, the process is carried out at a temperature greater than the glass transition temperature of the precursor web.

Optionally, the precursor web may be plasticized to make it less brittle prior to embossing in the process of the present invention.

In one embodiment, the precursor web is strain hardening. The strain hardening properties of the precursor web can be desirable to facilitate conformation of the precursor web to the discrete protruded elements of the forming structure in the process of the present invention. This can be preferred for producing embossed webs wherein closed distal ends of the extended elements of the embossed web are desired.

Precursor web can be any material, such as a polymeric film, having sufficient material properties to be formed into an embossed web described herein by the embossing process of the present invention. The precursor web will typically have a yield point and the precursor web is preferably stretched beyond its yield point by the process of the present invention to form an embossed web. That is, the precursor web should have sufficient yield properties such that the precursor web can be strained without rupture to an extent to produce the desired discrete extended elements with closed distal ends or, in the case of an embossed web comprising discrete extended elements having open distal ends, rupture to form open distal ends. As disclosed below, process conditions such as temperature can be varied for a given polymer to permit it to stretch with or without rupture to form the embossed web of the present invention comprising desired discrete extended elements. In general, therefore, it has been found that preferred starting materials to be used as the precursor web for producing the web of the present invention exhibit low yield and high-elongation characteristics. In addition, as discussed previously, the precursor webs preferably strain harden. Examples of films suitable for use as the precursor web in the process of the present invention include films comprising low density polyethylene (LDPE), linear low-density polyethylene (LLDPE), and blends of linear low-density polyethylene and low density polyethylene (LLDPE/LDPE).

Precursor web must also be sufficiently deformable and have sufficient ductility for use as a precursor web of the present invention. The term "deformable" as used herein describes a material which, when stretched beyond its elastic limit, will substantially retain its newly formed conformation, as well as exhibit thinning at or near the distal ends of the discrete extended elements of the resulting embossed web.

One material found suitable for use as a precursor web of the present invention is DOWLEX 2045A polyethylene resin, available from The Dow Chemical Company, Midland, Mich., USA. A film of this material having a thickness of 20 microns can have a tensile yield of at least 12 MPa; an ultimate tensile of at least 53 MPa; an ultimate elongation of at least 635%; and a tensile modulus (2% Secant) of at least 210 MPa (each of the above measures determined according to ASTM D 882). Other suitable precursor webs include polyethylene film that is about 25 microns (1.0 mil) thick and has a basis weight of about 24 grams per square meter ("gsm") available from available from RKW US and polyethylene/polypropylene film having a basis weight of about 14 gsm and a thickness of about 15 microns available from RKW US.

The precursor web can be a laminate of two or more webs, and can be a co-extruded laminate. For example, precursor web can comprise two layers, and precursor web can comprise three layers, wherein the innermost layer is referred to as a core layer, and the two outermost layers are referred to as skin layers. In one embodiment, the precursor web comprises a three layer coextruded laminate having an overall thickness of about 25 microns (0.001 in.), with the core layer having a thickness of about 18 microns (0.0007 in.); and each skin layer having a thickness of about 3.5 microns (0.00015 in.).

In one embodiment, the layers can comprise polymers having different stress-strain and/or elastic properties.

The precursor web can be made using conventional procedures for producing multilayer films on conventional coextruded film-making equipment. Where layers comprising blends are required, pellets of the above described components can be first dry blended and then melt mixed in the extruder feeding that layer. Alternatively, if insufficient mixing occurs in the extruder, the pellets can be first dry blended and then melt mixed in a pre-compounding extruder followed by repelletization prior to film extrusion. Suitable methods for making precursor web are disclosed in U.S. Pat. No. 5,520,875 and U.S. Pat. No. 6,228,462.

In general, the ability to form high area density (or low average center-to-center spacing) discrete extended elements on the embossed web can be limited by the thickness of precursor web. For example, in one embodiment, it is believed that the center-to-center spacing of two adjacent discrete extended elements should be greater than about twice the thickness of precursor web to permit adequate and complete three-dimensional embossed web formation between adjacent discrete protruded elements of the forming structure. In addition, in one embodiment, a ratio of the average height of the plurality of discrete protruded elements of the forming structure and the thickness of the precursor web will typically be at least about 1:1, at least about 2:1, at least about 3:1, at least about 4:1, or at least about 5:1.

In certain embodiments, the precursor web can optionally further comprise a surfactant. If utilized, preferred surfactants include those from non-ionic families such as: alcohol ethoxylates, alkylphenol ethoxylates, carboxylic acid esters, glycerol esters, polyoxyethylene esters of fatty acids, polyoxyethylene esters of aliphatic carboxylic acids related to abietic acid, anhydrosorbitol esters, ethoxylated anhydrosorbitol esters, ethoxylated natural fats, oils, and waxes, glycol esters of fatty acids, carboxylic amides, diethanolamine condensates, and polyalkyleneoxide block copolymers. Molecular weights of surfactants selected for the present invention may range from about 200 grams per mole to about 10,000 grams per mole. Preferred surfactants have a molecular weight from about 300 to about 1,000 grams per mole.

If utilized, the surfactant level initially blended into precursor web can be as much as 10 percent by weight of the total precursor web. Surfactants in the preferred molecular weight range (300-1,000 grams/mole) can be added at lower levels, generally at or below about 5 weight percent of the total precursor web.

In certain embodiments, the precursor web can also comprise titanium dioxide in the polymer blend. Titanium dioxide can provide for greater opacity of the embossed web. Titanium dioxide can be added at up to about 10 percent by weight of the precursor web, such as low density polyethylene.

Other additives, such as particulate material, e.g., particulate skin treatments or protectants, or odor-absorbing actives, e.g., zeolites, can optionally be added in one or more layers of precursor web. In some embodiments, embossed webs comprising particulate matter, when used in skin-contacting applications, can permit actives to contact the skin in a very direct and efficient manner. Specifically, in some embodiments, formation of discrete extended elements can expose particulate matter at or near the distal ends thereof. Therefore, actives such as skin care agents can be localized at or near distal ends of the discrete extended elements to permit direct skin contact with such skin care agents when the embossed web is used in skin contacting applications.

The average particle size of the particulate material, if utilized in the precursor web, will typically be from about 0.2 microns to about 200 microns, or from about 5 microns to about 100 microns. The use of certain particulate materials, such as mica particles, can dramatically improve the visual appearance of the embossed web.

The precursor web can also optionally include colorants, such as pigment, lake, toner, dye, ink or other agent used to impart a color to a material, to improve the visual appearance of the embossed web.

Suitable pigments herein include inorganic pigments, pearlescent pigments, interference pigments, and the like. Non-limiting examples of suitable pigments include talc, mica, magnesium carbonate, calcium carbonate, magnesium silicate, aluminum magnesium silicate, silica, titanium dioxide, zinc oxide, red iron oxide, yellow iron oxide, black iron oxide, carbon black, ultramarine, polyethylene powder, methacrylate powder, polystyrene powder, silk powder, crystalline cellulose, starch, titanated mica, iron oxide titanated mica, bismuth oxychloride, and the like.

Suitable colored webs are described in co-pending U.S. application Ser. No. 12/721,947, filed Mar. 11, 2010 entitled "COLORED WEB MATERIAL COMPRISING A PLURALITY OF DISCRETE EXTENDED ELEMENTS" (P&G Case 11634) and U.S. application Ser. No. 12/721,965, filed Mar. 11, 2010 entitled "WEB MATERIAL EXHIBITING VIEWING-ANGLE DEPENDENT COLOR AND COMPRISING A PLURALITY OF DISCRETE EXTENDED ELEMENTS" (P&G Case 11635).

The precursor web can also optionally include fillers, plasticizers, and the like.

Embossed Web

The precursor web is processed according to the process of the present invention to form an embossed web that can have various desired structural features and properties such as desired soft hand feel and an aesthetically pleasing visual appearance. The precursor web is positioned between the forming structure and compliant substrate and pressure is provided to conform the precursor web to the discrete protruded elements of the forming structure. An embossed web having certain structure is thereby produced.

In one embodiment, the embossed web resulting from the process described herein can have a structure similar to that described in detail in U.S. Pat. No. 7,402,723 or 7,521,588.

Figure 6:
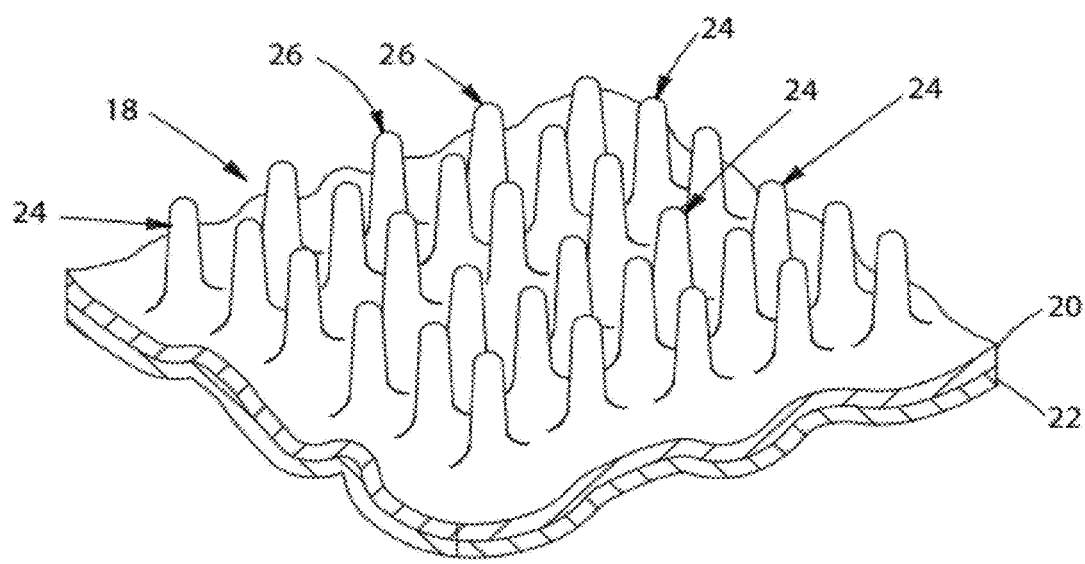
FIG. 6 is a perspective view of a portion of an embossed web of the present invention.

FIG. 6 is a partial view of one embodiment of a three-dimensional embossed web 18. The three-dimensional embossed web 18 is produced from a precursor web, which can be a single layer of web material or a multilayer coextruded or laminate web material as described hereinbefore. As shown in FIG. 6, the precursor web is a two layer laminate film comprising a first layer 20 and a second layer 22. Laminate film materials may be coextruded, as is known in the art for making laminate films, including films comprising skin layers.

FIG. 6 shows an embossed web 18 comprising a plurality of discrete extended elements 24. The discrete extended elements 24 are formed as protruded extensions of the web, generally on a first surface thereof. The number, size, and distribution of discrete extended elements 24 on the embossed web 18 can be predetermined based on desired soft feel, sound effects and visual effects. For applications such as a topsheet, backsheet or release paper wrapper in disposable absorbent articles, or packaging, it can be desired that the discrete extended elements 24 protrude only from one surface of embossed web 18. Therefore, when the embossed web 18 is used as a topsheet in a disposable absorbent article, the embossed web 18 can be oriented such that the discrete extended elements 24 are skin contacting for superior softness impression. Moreover, having discrete extended elements 24 with closed distal ends 26 can result in reduced rewet, i.e., reduced amounts of fluid being re-introduced to the surface of the topsheet after having been first passed through apertures of the topsheet to underlying absorbent layers (note that apertures, such as macroapertures, are not shown in the Figures herein).

FIG. 7 is a cross-sectional view of a portion of one embodiment of an embossed web 18 of the present invention. As shown in FIG. 7, discrete extended elements 24 can be described as protruding from first surface 28 of the embossed web 18. As such, the discrete extended elements 24 can be described as being integral with precursor web 30, and formed by permanent local plastic deformation of the precursor web 30. The discrete extended elements 24 can be described as having a side wall(s) 32 defining an open proximal portion 34 and a closed or open distal end 26. The discrete extended elements 24 each have a height h measured from a minimum amplitude $A_{min}$ between adjacent extended elements to a maximum amplitude $A_{max}$ at the closed or open distal end 26. The discrete extended elements have a diameter d, which for a generally cylindrical structure is the outside diameter at a lateral cross-section. By "lateral" is meant generally parallel to the plane of the first surface 28. For generally columnar discrete extended elements having non-uniform lateral cross-sections, and/or non-cylindrical structures of discrete extended elements, diameter d is measured as the average lateral cross-sectional dimension at ½ the height h of the discrete extended element, as shown in FIG. 7. Thus, for each discrete extended element 24, an aspect ratio, defined as h/d, can be determined. The discrete extended element 24 can have an aspect ratio h/d of at least about 0.2, at least about 0.3, at least about 0.5, at least about 0.75, at least about 1, at least about 1.5, at least about 2, at least about 2.5, or at least about 3. The discrete extended elements 24 will typically have a height h of at least about 30 microns, at least about 50 microns, at least about 65, at least about 80 microns, at least about 100 microns, at least about 120 microns, at least about 150 microns, or at least about 200 microns. The extended elements will typically be at least the same height as the thickness of the precursor web, or at least 2 times the thickness of the precursor web, or at least 3 times the thickness of the precursor web. The discrete extended elements 24 will typically have a diameter d of about 50 microns to about 5,000 microns, about 50 microns to about 3,000 microns, about 50 microns to about 500 microns, about 65 microns to about 300 microns, or about 75 microns to about 200 microns. In certain embodiments, the discrete extended elements 24 can have a larger diameter d up to about 2.5 centimeters, up to about 2 centimeters, up to about 1.5 centimeters, up to about 1 cm, up to about 0.5 centimeters, or up to about 0.1 centimeters.

For discrete extended elements that have generally non-columnar or irregular shapes, a diameter of the discrete extended element can be defined as two times the radius of gyration of the discrete extended element at ½ height.

For discrete extended elements that have shapes, such as ridges, that extend lengthwise across the entire web material such that the extended elements have a portion of the sidewalls of the extended elements that are open, a diameter of a discrete extended element can be defined as the average minimal width between two opposing sidewalls of the extended element at ½ height.

In general, because the actual height h of any individual discrete extended element 24 can be difficult to determine, and because the actual height may vary, an average height $h_{avg}$ of a plurality of discrete extended elements can be determined by determining an average minimum amplitude $A_{min}$ and an average maximum amplitude $A_{max}$ over a predetermined area of the embossed web 18. Such average height $hp_{avg}$ will typically fall within the ranges of heights described above Likewise, for varying cross-sectional dimensions, an average diameter $d_{avg}$ can be determined for a plurality of discrete extended elements 24. Such average diameter $d_{avg}$ will typically fall within the ranges of diameters described above. Such amplitude and other dimensional measurements can be made by any method known in the art, such as by computer aided scanning microscopy and data processing. Therefore, an average aspect ratio $AR_{avg}$ of the discrete extended elements 24 for a predetermined portion of the embossed web 18 can be expressed as $h_{avg}/d_{avg}$.

The dimensions h and d for the discrete extended elements 24 can be indirectly determined based on the known dimensions of a forming structure, if the precursor web 30 is fully conformed to the forming structure. For example, for a forming structure 8 made according to predetermined dimensions of male protrusions, e.g., the discrete protruded elements 10 shown in FIG. 1 on which the discrete extended elements 24 are to be formed, can have known dimensions. If the precursor web 30 is fully and permanently deformed over the discrete protruded elements 10 of the forming structure, then h and d can be calculated from these known dimensions, taking into account the thickness (t) of the precursor web 30, including predicted and/or observed web thinning. If the precursor web 30 is not fully formed over the discrete protruded elements 10 of the forming structure 8, then the height h of discrete extended elements 24 of the embossed web 18 will be less than the corresponding height of the discrete protruded elements 10.

In one embodiment, the diameter of a discrete extended element 24 is constant or decreases with increasing amplitude (amplitude increases to a maximum at closed or open distal end 26). As shown in FIG. 7, for example, the diameter, or average lateral cross-sectional dimension, of the discrete extended elements 24 can be a maximum at proximal portion 34 and the lateral cross-sectional dimension steadily decreases to distal end 26. This structure is believed to be desirable to help ensure the embossed web 18 can be readily removed from the forming structure 8.

As shown in FIG. 7, thinning of the precursor web 30 occurs due to the relatively deep drawing required to form high aspect ratio discrete extended elements 24. For example, thinning can be observed at or near the closed or open distal ends 26. By "observed" is meant that the thinning is distinct when viewed in magnified cross-section. Such thinning can be beneficial as the thinned portions offer little resistance to compression or shear when touched. For example, when a person touches the embossed web 18 on the side exhibiting discrete extended elements 24, the fingertips of the person first contact the closed or open distal ends 26 of the discrete extended elements 24. Due to the high aspect ratio of the discrete extended elements 24, and the wall thinning of the precursor web 30 at or near the distal ends 26, the discrete extended elements 24 offer little resistance to the compression or shear imposed on the embossed web by the person's fingers. This lack of resistance is registered as a feeling of softness, much like the feeling of a velour fabric.

Thinning of the precursor web at or near the closed or open distal ends 26 can be measured relative to the thickness of the precursor web or relative to the thickness of the land area that completely surrounds the discrete extended elements of the embossed web. The precursor web will typically exhibit thinning of at least about 25%, at least about 50%, or at least about 75% relative to the thickness of the precursor web. The precursor web will typically exhibit thinning of at least about 25%, at least about 50%, or at least about 75% relative to the thickness of the land area surrounding the discrete extended elements of the embossed web.

It should be noted that a fluid impermeable web having only the discrete extended elements as disclosed herein, and not having macroscopic apertures or discrete extended elements having open distal ends, can offer softness for any application in which fluid permeability is not required. Thus, in one embodiment of the present invention, the invention can be described as an embossed web exhibiting a soft and silky tactile impression on at least one surface thereof, the silky feeling surface of the embossed web exhibiting a pattern of discrete extended elements, each of the discrete extended elements being a protruded extension of the web surface and having a side wall defining an open proximal portion and a closed or open distal end, the discrete extended elements having a maximum lateral cross-sectional dimension at or near the open proximal portion.

The embossed web of the present invention can also exhibit improved sound effects. For example, when handled or manually manipulated, the embossed web creates less sound as compared to the precursor web. Optionally, certain embossment patterns can create distinctive, desirable sounds when touched or rubbed.

The "area density" of the discrete extended elements, which is the number of discrete extended elements per unit area of first surface, can be optimized and the embossed web will typically comprise from 4 to about 10,000, from about 95 to about 10,000, from about 240 to about 10,000, from about 350 to about 10,000, from about 500 to about 5,000, or from about 700 to about 3,000 discrete extended elements per square centimeter. In general, the center-to-center spacing can be optimized for adequate tactile impression, while at the same time minimizing entrapment of materials, such as fluids, between discrete extended elements. The center-to-center spacing between adjacent discrete extended elements can be from about 100 microns to about 1,020 microns, from about 30 to about 800, from about 100 microns to about 640 microns, from about 150 microns to about 500 microns, or from about 180 microns to about 430 microns.

Figure 8:
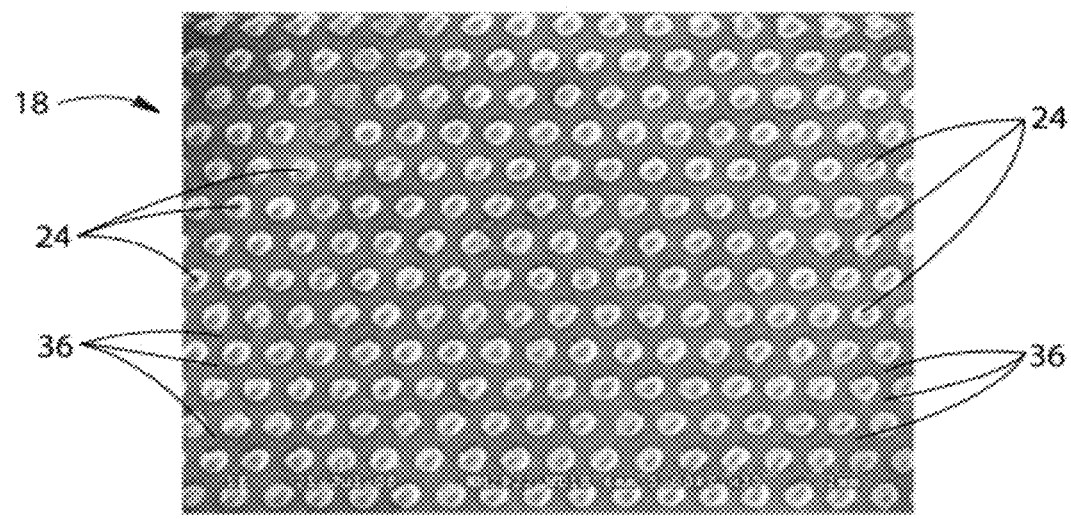
FIG. 8 is a photomicrograph showing a top view of an embossed web of the present invention.

FIG. 8 is a photomicrograph of a top view of one embodiment of an embossed web 18 of the present invention comprising a plurality of discrete extended elements 24 completely surrounded by land areas 36.

Figure 9:
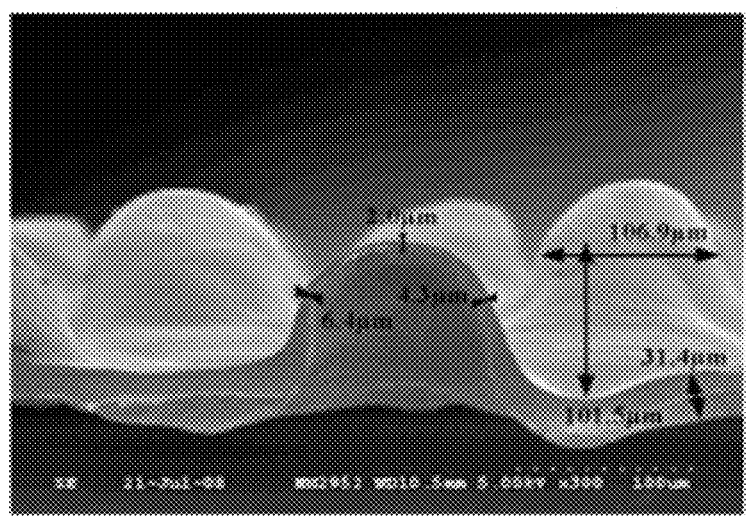
FIG. 9 is a photomicrograph showing a cross-sectional view of a portion of an embossed web of the present invention.

FIG. 9 is a photomicrograph of a cross-sectional view of one embodiment of an embossed web of the present invention which includes a cross-sectional view of a discrete extended element of the embossed web.

Figure 10:
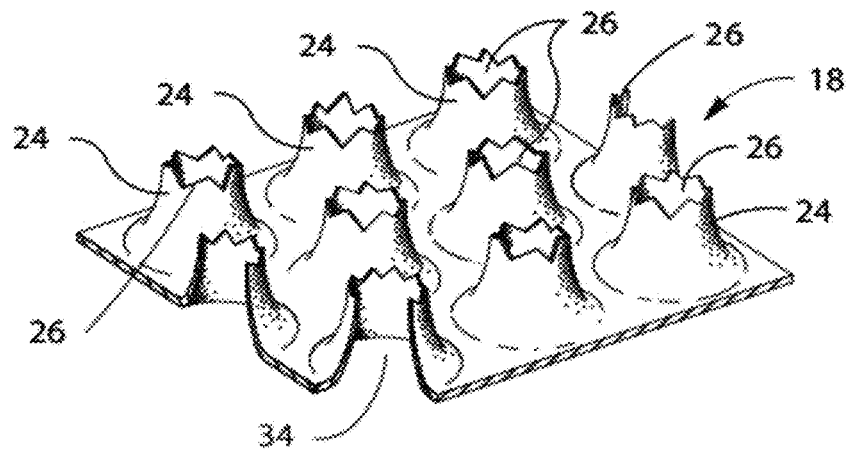
FIG. 10 is a perspective view of a portion of an embossed web of the present invention.

FIG. 10 illustrates one embodiment of an embossed web 18 of the present invention comprising a plurality of discrete extended elements 24, wherein the discrete extended elements 24 have open distal ends 26 and open proximal portions 34.

When the embossed web is utilized as a topsheet for disposable absorbent articles, the embossed web can further comprise macroapertures that allow fluid to flow through the embossed web.

Process for Making Embossed Web

The process of the present invention involves providing a forming structure as described herein, providing a compliant substrate as described herein, and generating a pressure between the forming structure and the compliant substrate. The process further involves providing a precursor web as described herein between the forming structure and the compliant substrate. The pressure between the forming structure and compliant substrate is sufficient to conform the precursor web to the forming structure to produce an embossed web. The conformation of the precursor web to the forming structure can be partial conformation, substantial conformation, or complete conformation, depending upon the pressure generated and the topography of the forming structure. While not being bound by theory, it is believed that open distal ends can be formed by the process of the present invention by locally rupturing the precursor web while conforming the precursor web to the protruded elements of the forming structure.

To get permanent deformation of the precursor web to form the embossed web of the present invention, the precursor web is typically stretched by the process of the present invention beyond the yield point of the precursor web.

Figure 11:
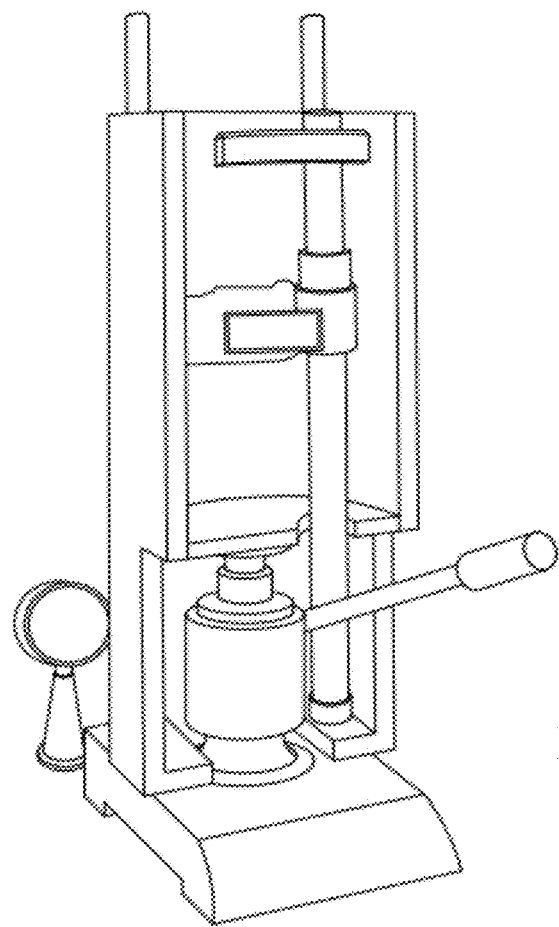
FIG. 11 is a perspective view of a hydraulic press utilized in a batch process for making an embossed web of the present invention.

The process of the present invention can be a batch process or a continuous process. A batch process can involve providing individual sheets of precursor web material that is placed between the forming structure and compliant substrate, each of which are typically in flat plate form. In one embodiment, the forming structure and compliant substrate are each in the form of flat plates which are placed in a hydraulic press or a clicker press. An example of a hydraulic press is available as Model C from Carver, Inc. Such a hydraulic press is shown in FIG. 11. The precursor web is placed between the forming structure plate and the compliant substrate plate and pressure is applied by the hydraulic press to conform the precursor web to the forming structure to produce an embossed web of the present invention.

Figure 12:
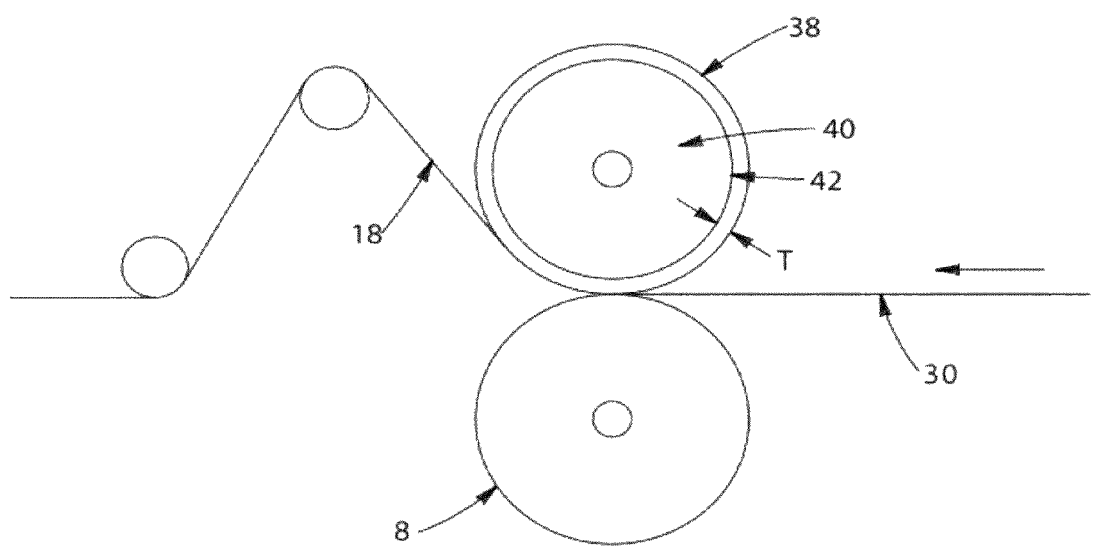
FIG. 12 is a schematic illustration of a continuous process for making an embossed web of the present invention.

A continuous process can involve providing a roll of precursor web material that is unwound and fed between the forming structure and compliant substrate, each of which can be in the form of a roll. FIG. 12 illustrates one embodiment of a continuous process of the present invention wherein a precursor web 30 is fed between a forming structure roll 8 and a compliant substrate roll 38. The compliant substrate roll 38 comprises a rigid roll 40, such as a steel roll, that is covered with a compliant material 42. The compliant material 42 has a thickness T of about 3 mm. As the precursor web passes between the forming structure roll 8 and the compliant substrate roll 38, an embossed web 18 is formed.

The process of the present invention can involve relatively short dwell times. As used herein, the term "dwell time" refers to the amount of time pressure is applied to a given portion of the precursor web, usually the amount of time a given portion of the precursor web spends positioned between the forming structure and compliant substrate. For a process of the present invention, pressure is typically applied to the precursor web for a dwell time of less than about 5 seconds, less than about 1 second, less than about 0.01 second, less than about 0.005 second, or less than about 0.002 second. For example, the dwell time can be about 0.5 milliseconds to about 50 milliseconds.

Even with such relatively short dwell times, embossed webs can be produced with desirable structural features described herein. As a result, the process of the present invention enables high speed production of embossed webs.

For a process of the present invention, especially for a continuous process, the precursor web can be fed between the forming structure and the compliant substrate at a rate of at least about 0.01 meters per second, at least about 1 meter per second, at least about 5 meters per second, at least about 7 meters per second, or at least about 10 meters per second. Other suitable rates include, for example, at least about 0.01, 0.05, 0.1, 0.5, 1, 2, 3, 4, 5, 6, 7, 8, 9, or 10 meters per second.

Depending upon factors such as the shape of the protrusions on the forming structure and the pressure applied, the distal ends of the extended elements of the embossed web produced by the process of the present invention can be either closed or open.

The process of the present invention can be carried out at ambient temperature, meaning that no heat is intentionally applied to the forming structure, compliant substrate, and/or precursor web. It should be recognized, however, that heat can be generated due to the pressure between the forming structure and the compliant substrate, especially in a continuous process. As a result, the forming structure and/or the compliant substrate may be cooled in order to maintain the process conditions at the desired temperature, such as ambient temperature, and to improve durability of the compliant substrate.

The process can also be carried out with the precursor web 34 having an elevated temperature. For example, the temperature of the precursor web 34 can be less than the melting point of the precursor web 34. For example, the temperature of the precursor web 34 can be at least about 10° C. below the melting point of the precursor web 34. The precursor web 34, especially a precursor web 34 including polyethylenes, can have a temperature during the process of about 10° C. to about 120° C., about 20° C. to about 110° C., about 10° C. to about 80° C., or about 10° C. to about 40° C. The precursor web 34 can be heated during the process by heating the precursor web 34, the compliant substrate 36, and/or the forming structure 10.

In one embodiment, the precursor web is not heated before being provided between the forming structure and the compliant substrate. In another embodiment, the precursor web, the forming structure and the compliant substrate are not heated before providing the precursor web between the forming structure and the compliant substrate.

In general, the process of the present invention can be carried out at a temperature of from about 10° C. to about 200° C., from about 10° C. to about 120° C., from about 10° C. to about 80° C., or from about 10° C. to about 40° C. The temperature at which the process of the present invention is carried out can be measured by, for example, a non-contact thermometer, such as an infrared thermometer or a laser thermometer, measuring the temperature at the nip between the compliant substrate and forming structure. The temperature can also be determined using temperature sensitive material such as Thermolabel available from Paper Thermometer Company. In one embodiment, the process is carried out at a temperature less than the melting point of the precursor web. In one embodiment, the process is carried out at a temperature greater than the glass transition temperature of the precursor web.

In the process of the present invention, an average pressure is provided between the compliant substrate and the forming structure. The average pressure is sufficient to conform the precursor web, which is positioned between the forming structure and compliant substrate, to the discrete protruded elements of the forming structure to form an embossed web of the present invention. In general, the average pressure provided between the forming structure and compliant substrate will be from about 50 to about 10,000 pounds per square inch ("psi") (i.e. from about 0.3 to about 68.9 MPa), from about 100 to about 5,000 psi (i.e. from about 0.7 to about 34.5 MPa), from about 100 to about 3,500 psi (i.e. from about 0.7 to about 24.1 MPa), or from about 200 to about 2,500 psi (i.e. from about 1.4 to about 17.2 MPa).

The average pressure provided between the forming structure and the compliant substrate can be determined as a force per unit area. A force is applied to the forming structure and/or compliant substrate so that the forming structure and compliant substrate become engaged to a desired depth of engagement, as described hereinbelow. The unit area is the area of the "contact patch" between the forming structure and the compliant substrate. From these values, an average pressure between the forming structure and compliant substrate can be calculated.

If the forming structure and compliant substrate are both flat plates, the area of the contact patch between the forming structure and compliant substrate is typically easily determined based on the dimensions of the flat plates.

If the forming structure and the compliant substrate are both rolls, the area of the contract patch between the forming structure and compliant substrate can be determined by static loading of the rolls with a piece of pressure sensitive film provided between the rolls. A suitable pressure sensitive film is Fuji Prescale Film available from FUJIFILM NDT Systems, which undergoes certain color changes upon application of pressure to the film. The static loading on the rolls is released and the pressure sensitive film is removed from the rolls. The pressure sensitive film will have a color-changed area that represents the contact patch between the forming structure and compliant substrate. Using this contact patch area and the force applied to the forming structure roll and/or compliant structure roll, the average pressure provided between the forming structure roll and compliant structure roll can be calculated.

The forming structure and compliant substrate are engaged to a desired depth of engagement by applying a force to the forming structure and/or compliant substrate. The "depth of engagement" is determined by measuring the distance the forming structure is pressed into the compliant substrate. This distance can be measured by bringing the forming structure and compliant substrate into initial contact and then forcing the forming structure and compliant substrate together. The distance that the forming structure and compliant substrate are moved relative to each other subsequent to the initial contact is referred to as the "depth of engagement". If the forming structure and compliant substrate are both rolls, the depth of engagement can be measured as the change in distance between the rotational axis of the forming structure and the rotational axis of the compliant substrate due to the force applied after initial contact.

For the process of the present invention, the depth of engagement between the forming structure and the compliant substrate will typically be from about 0.1 mm to about 5 mm, from about 0.2 mm to about 4 mm, or from about 0.3 mm to about 3 mm.

The forming structure and compliant substrate of the present invention can be utilized in a low strain rate process, such as that described in U.S. Application No. 2008/0224351 A1, to produce an embossed web of the present invention. Such a process is encompassed by the present invention.

The process of the present invention can optionally further comprise the step of applying a slip agent to the precursor web, forming structure, and/or compliant substrate before the precursor web is provided between the forming structure and the compliant substrate. The can be beneficial, especially in a continuous process, to reduce friction between the precursor web, the forming structure, and/or the compliant substrate. Non-limiting examples of suitable slip agents include silicone, talc, lubricating oils, and the like.

The process of the present invention can optionally be combined with other processes to further manipulate the embossed web. In one embodiment, such additional processes can be combined with the process of the present invention on the same process manufacturing line to produce, for example, absorbent articles. In one embodiment, the process of the present invention is combined with a process that can impart macroapertures in the embossed web, such as the process described in US 2006/0087053 A1 or US 2005/0064136 A1. Such a process combination can produce a macroapertured embossed web that can be suitable for use as a topsheet in an absorbent article. Such a macroapertured embossed web can be subsequently converted into an absorbent article by combining it with other absorbent article components, such as absorbent cores, backsheets, and the like, preferably on the same process manufacturing line.

In addition to the processes described hereinbefore, alternative processes for making embossed webs are contemplated. The process can further include applying pressure from a second pressure source, e.g. a pressure source in addition to the first compliant substrate. The second pressure source can be selected from the group consisting of a static liquid pressure plenum, a static gas pressure plenum, a velocity gas pressure source, such as an air knife, a velocity liquid pressure source, such as is used in conventional hydroforming process, and a compliant substrate. Co-pending U.S. patent application Ser. No. 12/721,989, filed Mar. 11, 2010 entitled "PROCESS FOR MAKING AN EMBOSSED WEB" (P&G Case 11636), discloses a suitable static pressure plenum for use in the process of the present disclosure. Other suitable static pressure plenums for use in the process of the present disclosure include those described in U.S. Provisional Patent Application Ser. No. 61/313,122, filed Mar. 11, 2010 entitled "APPARATUS FOR EMBOSSING A WEB" (P&G Case 11639P), and in U.S. Pat. No. 5,972,280. The pressures exerted on the precursor web by the second pressure source will typically be similar to those pressures exerted on the precursor web by the compliant substrate described hereinbefore. The second pressure source can apply a pressure against the precursor web before or after the compliant substrate. In one embodiment, at least two compliant substrates are provided and pressure is applied on a first portion of the precursor web between the forming structure and the first compliant substrate. Pressure can then be applied on the first portion of the precursor web between the forming structure and the second compliant substrate. This can further conform the portion of the precursor web registered to the same discrete protruded elements of the forming structure. This can allow for enhancement of the discrete extended elements formed by the process.

Alternative Processes for Making Embossed Webs

In addition to the processes described hereinbefore, alternative processes for making embossed webs are contemplated. For example, the compliant substrate described herein can be replaced by other ways of imparting force or pressure to conform the precursor web to the forming structure.

In an alternative embodiment, the compliant substrate can be replaced with fluid pressure, such as air pressure or water pressure. The pressures exerted on the precursor web by fluids such as air or water will typically be similar to those pressures exerted on the precursor web by the compliant substrate described hereinbefore.

One example of a device suitable for providing air pressure to conform the precursor web to the forming structure of the present invention is a high pressure air knife High pressure air knives are commercially available from, for example, Canadian Air Systems.

An example of a device suitable for providing water pressure to conform the precursor web to the forming structure of the present invention is a water plenum, such as that described in U.S. Pat. No. 7,364,687.

The process of the present invention can also be utilized to emboss together two or more separate precursor webs. In this regard, the process of the present invention can result in the precursor webs being mechanically bonded together by friction between the precursor webs after being embossed together. Such mechanical bonds can be strong enough for many applications requiring two or more precursor webs to be sealed together. Also, for applications which require releasable seals, such a mechanical bond, when released by tearing apart the embossed webs, tends to generate less noise or sound than with other types of bonds, such as thermal bonding.

Uses of Embossed Web

The embossed webs of the present invention can be utilized in a number of different ways, including as component materials of absorbent articles (such as topsheets, backsheets or release paper wrappers), packaging (such as flow wrap, shrink wrap, or polybags), trash bags, food wrap, dental floss, wipes, electronic components, wall paper, clothing, aprons, window coverings, placemats, book covers, and the like.

EXAMPLES

The following non-limiting examples demonstrate the impact of several variables on the average height of the discrete extended elements of the embossed webs of the present invention.

Examples 1-15

Effect of Temperature and Pressure

Fifteen embossed webs are produced under various pressures and temperatures—utilizing the same forming structure, compliant substrate, and precursor web—to determine the effects of pressure and temperature on the average height of the discrete extended elements of the embossed web.

The forming structure utilized is made by laser engraving a 3.2 mm (⅛") thick polyacetal sheet to form a plurality of discrete protruded elements in the polyacetal sheet. The discrete protruded elements are evenly spaced along the surface of the polyacetal sheet. The discrete protruded elements have tapered sidewalls with rounded tips (having a radius of about 50 microns (i.e. 2 mil)) and have an average height of about 270 microns, an average diameter (at half height) of about 100 microns, and center-to-center spacing of adjacent discrete protruded elements of about 254 microns (10 mil). The size of the forming structure is 5 cm×5 cm (2"×2").

The compliant substrate utilized is an EPDM rubber sheet that is 6.4 mm (¼") thick and has a Shore A hardness of 40 durometer is obtained from McMaster Can Company. Rubber hardness is confirmed with a Model 306 Type A Classic Style Durometer available from PTC Instruments of Los Angeles, Calif. The size of the compliant substrate is 5 cm×5 cm (2"×2").

The precursor web utilized is a polyethylene film obtained from RKW Company that is 1.0 mil thick and has a basis weight of 24.2 grams per square meter ("gsm").

A hydraulic press (Carver Model C available from Carver, Inc.) is used to emboss the precursor web. The compliant substrate is placed in the hydraulic press and heated to a specified temperature as measured by a laser thermometer (TELTRU model QTL1 05986). Within 5 seconds, the precursor web is placed on the compliant substrate, the forming structure is placed on the precursor web, and then pressure is applied by the press arm of the hydraulic press for about 3-5 seconds (dwell time). The pressure is read from the pressure gauge on the hydraulic press. The pressure is controlled to within about ±0.5 MPa (±75 psi), and the dwell time is controlled to within about ±2 seconds. For the examples involving elevated temperatures, the temperature is controlled to within about ±15° C.

Fifteen embossed webs are produced using different combinations of temperature and pressure. The average height of the discrete extended elements of each embossed web is measured manually using a MikroCAD compact micro-optical 3D measuring device (ODSCAD 4.0 manual) available from GFMesstechnik GmbH of Berlin, Germany. For each embossed web, the average height of about 100-125 discrete extended elements is measured and the standard deviation calculated.

Figure 13:
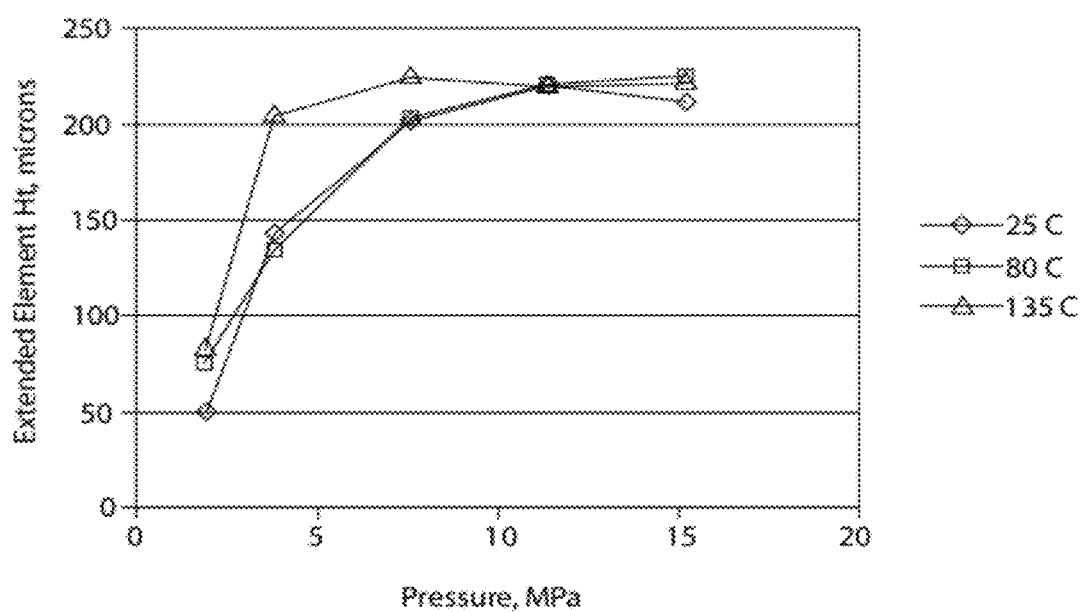
FIG. 13 is a line graph illustrating the effect of pressure and temperature on the average height of the discrete extended elements of an embossed web of the present invention.

The average height of the discrete extended elements for each embossed web is plotted as a line graph as shown in FIG. 13. This data shows that pressure has a much greater impact on extended element height than temperature. That is, even at 25° C., extended elements having heights similar to those produced at 135° C. can be made.

Examples 16-20

Effect of Film Type and Basis Weight

Five embossed webs are produced under various pressures to determine the effect of pressure on the average height of the discrete extended elements of the embossed web.

The forming structure and compliant substrate utilized are the same as those utilized in Examples 1-15 above.

The precursor web utilized is a polyethylene/polypropylene film having a basis weight of about 14 gsm and a thickness of about 15 microns (available from RKW).

The embossed webs are made using the hydraulic press and method of Example 1, except that in making each embossed web, the process is carried out at a temperature of 25 C.

Five embossed webs are produced under various pressures. The pressure for producing each web is controlled to within about ±0.5 MPa (±75 psi). The average height of the discrete extended elements of each embossed web is measured as in Examples 1-15 above.

Figure 14:
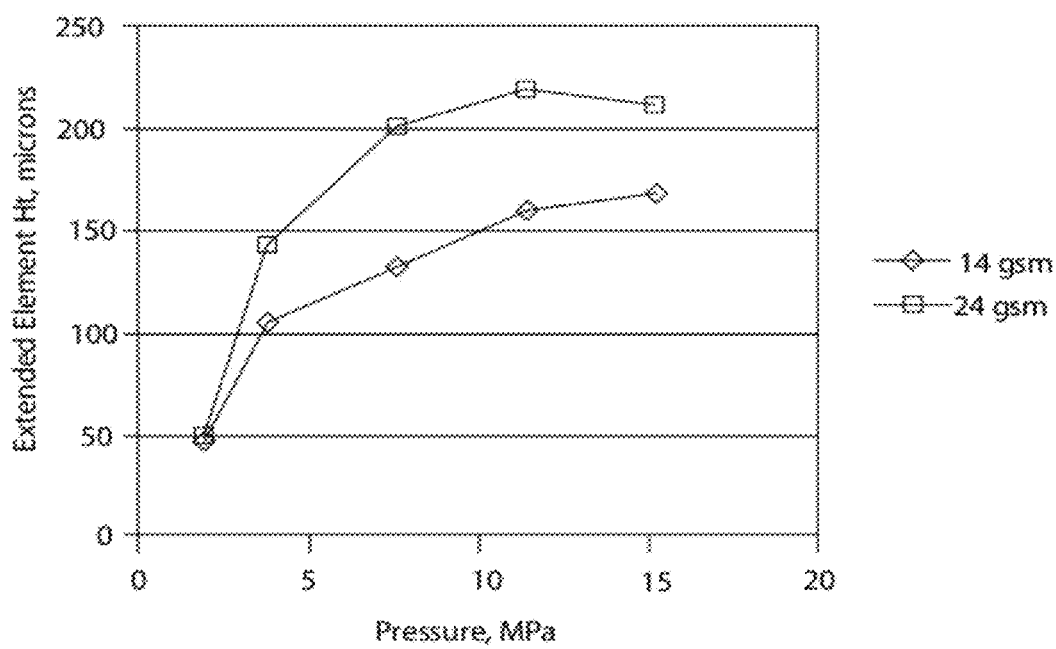
FIG. 14 is a line graph illustrating the effect of pressure on the average height of the discrete extended elements of embossed webs of the present invention made from precursor webs of differing basis weights.

The average height of the discrete extended elements for each embossed web is plotted as a line graph as shown in FIG. 14. This data shows that lower basis weight, polypropylene-containing films, tend to exhibit shorter extended elements under the same pressure as compared to higher basis weight, polyethylene-only films.

Examples 21-48

Effect of Compliant Substrate Hardness

Twenty-eight embossed webs are produced under various pressures and using compliant substrates having different Shore A hardness values to determine the effect on the average height of the discrete extended elements of the embossed web.

The forming structure is the same as that used in Examples 1-15 above.

The complaint substrate used is an EPDM rubber sheet that is 6.4 mm (¼") thick, the compliant substrates having different Shore A hardness values.

The precursor web utilized is the same as that utilized in Examples 1-15 above.

The embossed webs are made using the hydraulic press and method of Example 1, except that in making each embossed web, the process is carried out at a temperature of 25 C.

Twenty-eight embossed webs are produced under various pressures. The pressure for producing each web is controlled to within about ±0.5 MPa (±75 psi). The average height of the discrete extended elements of each embossed web is measured as in Examples 1-15 above.

Figure 15:
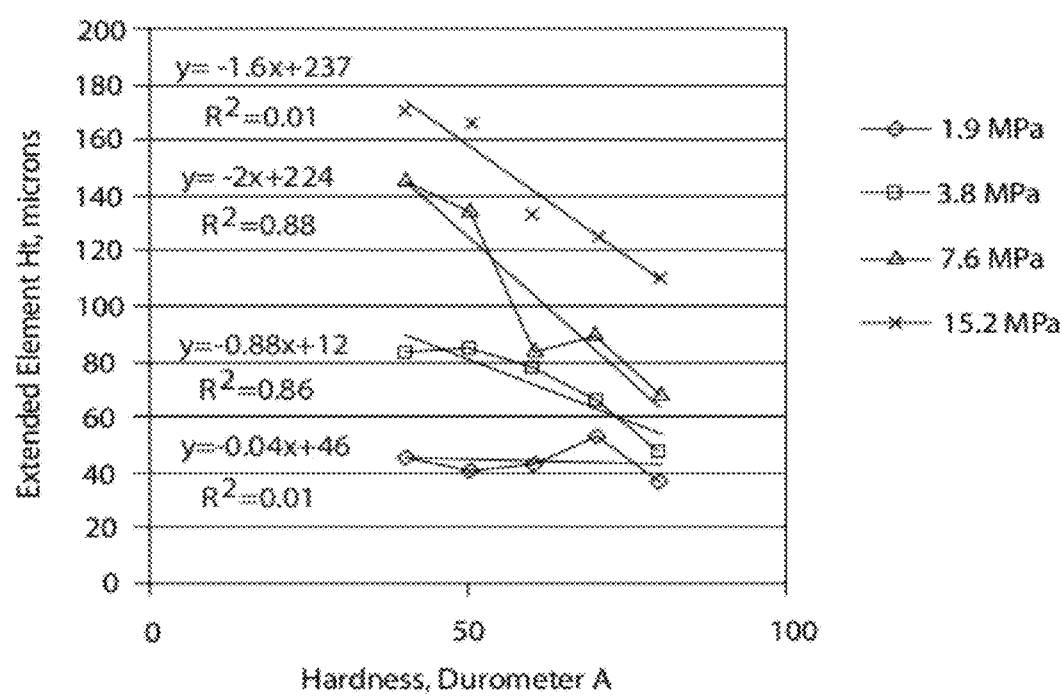
FIG. 15 is a line graph illustrating the effect of compliant substrate hardness at various pressures on the average height of the discrete extended elements of an embossed web of the present invention.

The average height of the discrete extended elements for each embossed web is plotted as a line graph as shown in FIG. 15. This data shows that softer compliant substrates tend to produce taller extended elements of the embossed webs, especially at higher pressures.

Examples 49-68

Effect of Compliant Substrate Thickness and Type

Twenty embossed webs are produced under various pressures and using compliant materials of different rubber types and thicknesses, each having the same Shore A hardness value, to determine the effect on the average height of the discrete extended elements of the embossed web.

The forming structure is the same as that used in Examples 1-15 above.

The compliant substrate is an EPDM rubber sheet or a gum rubber sheet of various thicknesses, the compliant substrates each having a Shore A hardness value of 40 durometer.

The precursor web utilized is the same as that utilized in Examples 1-15 above.

The embossed webs are made using the hydraulic press and method of Example 1, except that in making each embossed web, the process is carried out at a temperature of 25 C.

Twenty embossed webs are produced under various pressures. The pressure for producing each web is controlled to within about ±0.5 MPa (±75 psi). The average height of the discrete extended elements of each embossed web is measured as in Examples 1-15 above.

Figure 16A:
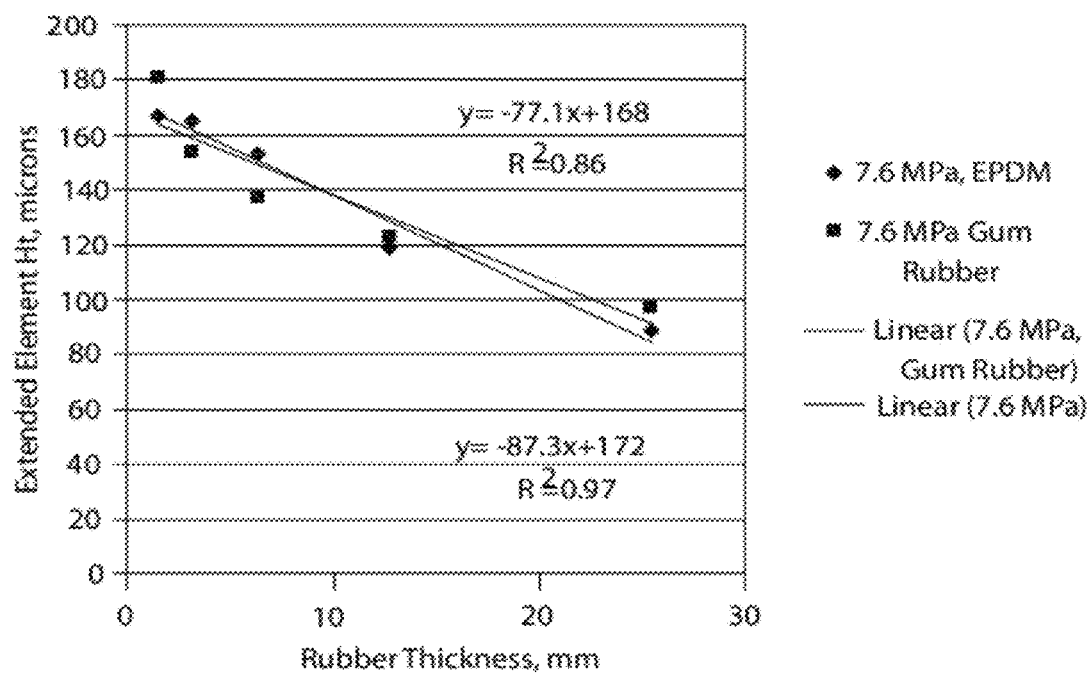
FIGS. 16A and 16B are line graphs illustrating the effect of compliant substrate thickness on the average height of the discrete extended elements of an embossed web of the present invention.
Figure 16B:
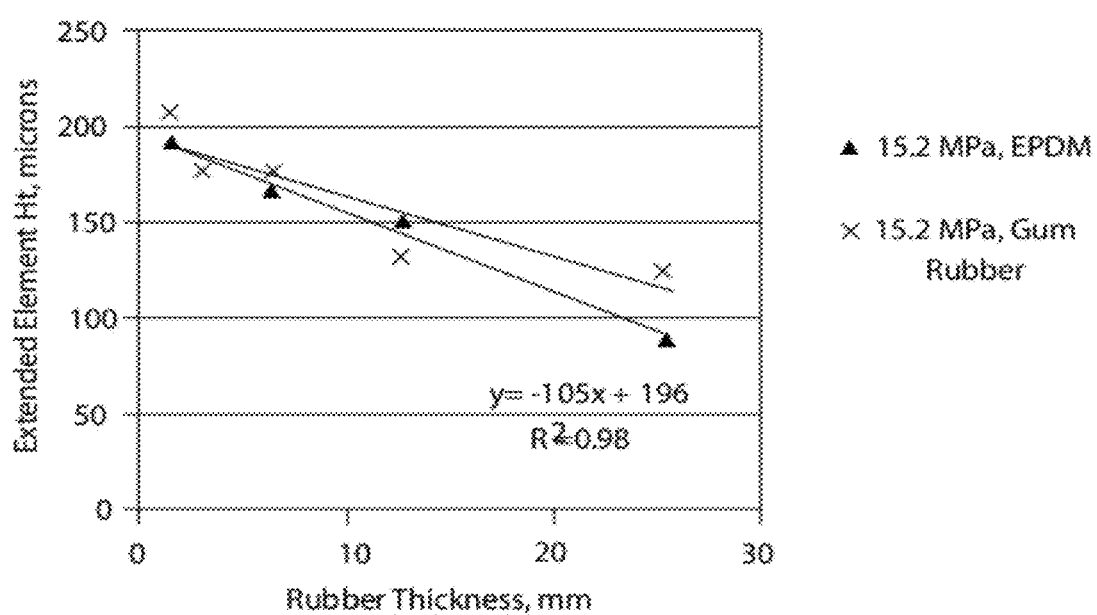

The average height of the discrete extended elements for each embossed web is plotted as line graphs as shown in FIGS. 16A and 16B. This data shows that for a given pressure, thinner compliant substrates tend to produce taller extended elements. It also shows that there is relatively little difference in bubble heights for two different rubber types of the same hardness and thickness.

Examples 69-87

Simulated Effect of Process Speed and Depth of Engagement

Nineteen embossed webs are produced using a high speed research press to simulate the effect of producing embossed webs under different process speeds and depths of engagement between the forming structure and the compliant substrate.

The forming structure is the same as that used in Examples 1-15 above.

The compliant substrate is a gum rubber sheet having a thickness of 0.25 inch (6.4 mm) and a Shore A hardness of 40 durometer.

The precursor web utilized is the same as that utilized in Examples 16-20 above.

A high speed research press is used to emboss the precursor web. The high speed research press utilized is described in detail in U.S. application Ser. No. 11/937,034 filed Nov. 8, 2007 and entitled "Research Press" (P&G Case 10949). The high speed research press is designed to simulate a continuous production line with respect to deforming the precursor web.

Fifteen embossed webs are produced using the high speed research press at rates of compression of 2.74 m/s or 7 m/s, and various depths of engagement ranging from 0.2 mm to 1.25 mm. The process temperature is either 150° C. or 25° C., and is controlled to within about ±20° C. for the higher temperature experiments.

Figure 17A:
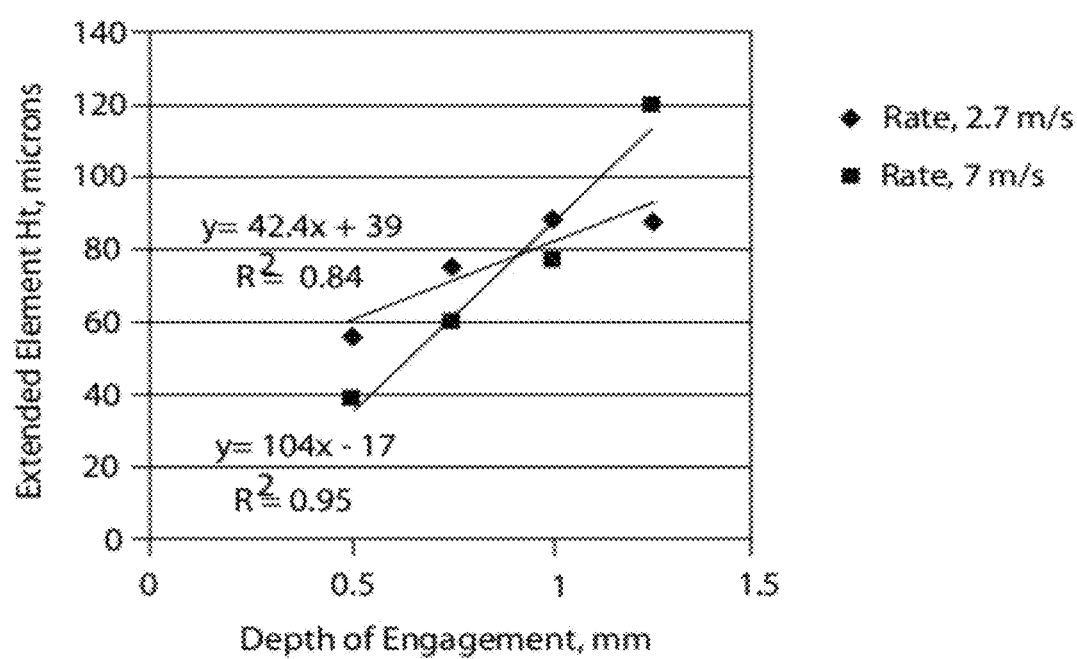
FIGS. 17A and 17B are line graphs illustrating the effect of producing embossed webs at different process speeds and depths of engagement between the forming structure and the compliant substrate.
Figure 17B:
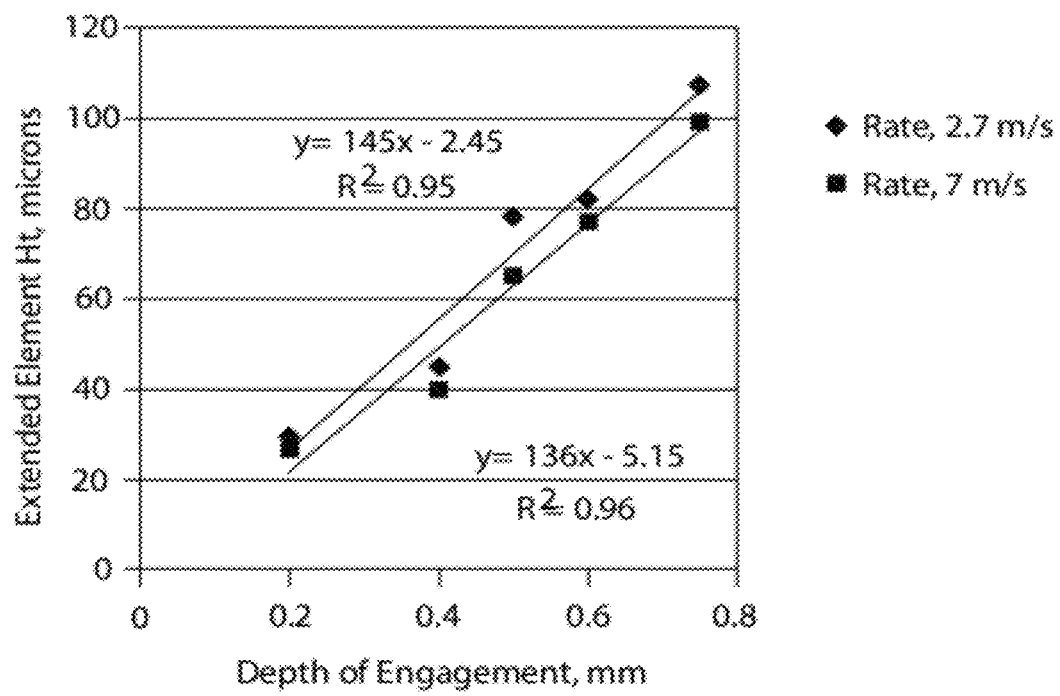

The average height of the discrete extended elements for each embossed web is plotted as line graphs as shown in FIGS. 17A and 17B. This data shows that the heights of the extended elements increase with increasing depth of engagement and there is relatively little impact of formation speed on extended element height. Also, even at 25° C., and 7 m/s rate, extended elements in the desired 100 micron range can be formed.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

When a technical feature is disclosed herein in relation to one embodiment, this feature can be combined with any other feature(s) disclosed in other embodiment(s) or claim(s), unless stated otherwise.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for making an embossed web comprising a plurality of discrete extended elements formed integrally with said embossed web, said extended elements having open proximal portions, closed or open distal ends, and sidewalls, said extended elements being thinned at said distal ends and/or along said sidewalls, said process comprising the steps of:
   providing a forming structure comprising a plurality of discrete protruded elements and lands completely surrounding said discrete protruded elements, wherein said discrete protruded elements each have a diameter of less than about 500 microns;
   providing a compliant substrate;
   providing a precursor web between said compliant substrate and said forming structure; wherein said precursor web comprises a colorant, synthetic material, metallic material, biological material, or combinations thereof; and
   said compliant substrate providing pressure against said forming structure sufficient to conform said precursor web to said discrete protruded elements of said forming structure to form said embossed web;
   wherein said precursor web has a melting point and wherein said process is carried out at a temperature less than said melting point of said precursor web;
   wherein said embossed web is formed and wherein said extended elements extend outwardly from a surface of said embossed web to a height that is greater than the thickness of said precursor web.

2. A process for making an embossed web comprising a plurality of discrete extended elements formed integrally with said embossed web, said extended elements having open proximal portions, closed or open distal ends, and sidewalls, said extended elements being thinned at said distal ends and/or along said sidewalls, said process comprising the steps of:
   providing a forming structure comprising a plurality of discrete protruded elements and lands completely surrounding said discrete protruded elements, wherein said forming structure comprises at least about 95 discrete protruded elements per square centimeter;
   providing a compliant substrate;
   providing a precursor web between said compliant substrate and said forming structure;
   wherein said precursor web comprises a colorant, synthetic material, metallic material, biological material, or combinations thereof; and
   said compliant substrate providing pressure against said forming structure sufficient to conform said precursor web to said discrete protruded elements of said forming structure to form said embossed web;
   wherein said precursor web has a melting point and wherein said process is carried out at a temperature less than said melting point of said precursor web;
   wherein said embossed web is formed and wherein said extended elements extend outwardly from a surface of said embossed web to a height that is greater than the thickness of said precursor web.

3. A process for making an embossed web comprising a plurality of discrete extended elements formed integrally with said embossed web, said extended elements having open proximal portions, closed or open distal ends, and sidewalls, said extended elements being thinned at said distal ends and/or along said sidewalls, said process comprising the steps of:
   providing a forming structure comprising a plurality of discrete protruded elements and lands completely surrounding said discrete protruded elements, wherein said discrete protruded elements each have a non-columnar shape;
   providing a compliant substrate;
   providing a precursor web between said compliant substrate and said forming structure; wherein said precursor web comprises a colorant, synthetic material, metallic material, biological material, or combinations thereof; and said compliant substrate providing pressure against said forming structure sufficient to conform said precursor web to said discrete protruded elements of said forming structure to form said embossed web;
   wherein said precursor web has a melting point and wherein said process is carried out at a temperature less than said melting point of said precursor web;
   wherein said embossed web is formed and wherein said extended elements extend outwardly from a surface of said embossed web to a height that is greater than the thickness of said precursor web.

4. The process of claim 1, wherein said precursor web is fed between said compliant substrate and said forming structure at a rate of at least about 0.01 meters per second.

5. The process of claim 1, wherein said pressure is applied to a given portion of said precursor web for a dwell time of from about 0.5 milliseconds to about 5 seconds.

6. The process of claim 1, wherein said process is carried out at a temperature of from about 10° C. to about 40° C.

7. The process of claim 1, wherein said precursor web is a thermoplastic film comprising polyethylene, polypropylene, or mixtures thereof.

8. The process of claim 1, wherein said compliant substrate comprises rubber having a Shore A hardness of from about 30 to about 80 durometer.

9. The process of claim 1, wherein said compliant substrate is in the form of a roll and said forming structure is in the form of a roll.

10. The process of claim 1, wherein said discrete protruded elements each have a generally columnar shape and an aspect ratio of at least about 0.5.

11. The process of claim 1, wherein said discrete protruded elements have an average edge-to-edge spacing of from about 30 microns to about 650 microns.

12. The process of claim 1, wherein said precursor web has a thickness of from about 5 microns to about 150 microns.

13. The process of claim 1, wherein said extended elements are thinned relative to said thickness of said precursor web.

14. The process of claim 1, wherein said distal ends of said extended elements are closed.

15. The process of claim 1, wherein said distal ends of said extended elements are open.

16. The process of claim 1, wherein said precursor web has a yield point, wherein said precursor web is stretched beyond said yield point by said process.

17. The process of claim 1, wherein said colorant is provided on at least a portion of the web and is selected from the group consisting of pigments, lakes, toners, dyes, ink, or combinations thereof.

18. The process of claim 2, wherein said colorant is provided on at least a portion of the web and is selected from the group consisting of pigments, lakes, toners, dyes, ink, or combinations thereof.

19. The process of claim 3, wherein said colorant is provided on at least a portion of the web and is selected from the group consisting of pigments, lakes, toners, dyes, ink, or combinations thereof.

20. The process of claim 1, wherein said plurality of discrete protruded elements comprise sidewalls having a degree of taper from about 5° to about 25°.

21. The process of claim 1, wherein said distal ends of at least some of said extended elements are closed.

22. The process of claim 1, wherein said plurality of discrete protruded elements comprise sidewalls having a degree of taper from about 5° to about 25° and wherein said compliant substrate comprises a non-recessed flat surface.

* * * * *